US012708545B2

(12) United States Patent
Miller et al.

(10) Patent No.: US 12,708,545 B2
(45) Date of Patent: Aug. 18, 2026

(54) EXPANDABLE SOCKET LINER

(71) Applicant: Icarus Medical, LLC, Charlottesville, VA (US)

(72) Inventors: Philip Miller, Charlottesville, VA (US); David T. Johnson, Charlottesville, VA (US); Evan Eckersley, Charlottesville, VA (US); George Miroulis, Virginia Beach, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 249 days.

(21) Appl. No.: 18/739,242

(22) Filed: Jun. 10, 2024

(65) Prior Publication Data

US 2024/0325187 A1 Oct. 3, 2024

Related U.S. Application Data

(60) Continuation-in-part of application No. 18/387,433, filed on Nov. 6, 2023, now Pat. No. 12,144,757, which is a continuation of application No. 18/075,203, filed on Dec. 5, 2022, now Pat. No. 11,806,264, which is a continuation-in-part of application No. 17/902,683, filed on Sep. 2, 2022, now Pat. No. 11,612,506, and a continuation-in-part of application No. 17/864,675, filed on Jul. 14, 2022, and a continuation-in-part of application No. PCT/US2022/021822, filed on Mar. 24, 2022, said application No. 17/864,675 is a continuation-in-part (Continued)

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 13/048; A61F 13/107; A61F 2013/49096; A61F 5/01; A61F 5/026; A61F 5/028; A61F 2/30; A61F 2002/30624
See application file for complete search history.

(56) References Cited

U.S. PATENT DOCUMENTS 4,433,456 A 2/1984 Baggio
4,748,726 A 6/1988 Schoch (Continued)

FOREIGN PATENT DOCUMENTS

WO 2009029191 A2 3/2009
WO 2014036471 A2 3/2014

(Continued)

OTHER PUBLICATIONS

Application No. PCT/US 23/82610, International Search Report and Written Opinion dated May 10, 2024.

(Continued)

*Primary Examiner* — Tarla R Patel
(74) *Attorney, Agent, or Firm* — Woods Rogers Vandeventer Black PLC; Nathan A. Evans

(57) ABSTRACT

A tension adjustment mechanism transforming the rotation of a dial into a change of volume of a worn-article, such as a prosthetic socket, to improve the fit of the worn-article.

25 Claims, 19 Drawing Sheets

Related U.S. Application Data of application No. 17/700,479, filed on Mar. 21, 2022, now Pat. No. 11,458,034, which is a continuation-in-part of application No. 17/537,476, filed on Nov. 29, 2021, now Pat. No. 11,666,472, said application No. 17/902,683 is a continuation of application No. 17/211,590, filed on Mar. 24, 2021, now Pat. No. 11,135,081, said application No. 17/537,476 is a continuation-in-part of application No. 17/211,635, filed on Mar. 24, 2021, now Pat. No. 11,819,436, and a continuation-in-part of application No. 17/074,571, filed on Oct. 19, 2020, now Pat. No. 12,059,383, said application No. 17/211,635 is a continuation of application No. 17/074,542, filed on Oct. 19, 2020, now Pat. No. 11,564,824, said application No. 18/075,203 is a continuation-in-part of application No. PCT/US2020/047904, filed on Aug. 26, 2020, said application No. 17/074,571 is a continuation-in-part of application No. 15/585,968, filed on May 3, 2017, now Pat. No. 10,806,619, said application No. 17/074,542 is a division of application No. 15/585,968, filed on May 3, 2017, now Pat. No. 10,806,619.

(60) Provisional application No. 63/394,530, filed on Aug. 2, 2022, provisional application No. 62/331,315, filed on May 3, 2016.

(56) References Cited

U.S. PATENT DOCUMENTS 4,790,081 A 12/1988 Benoit et al.
4,870,723 A 10/1989 Pozzobon et al.
5,341,583 A 8/1994 Hallenbeck
5,600,874 A 2/1997 Jungkind
5,606,778 A 3/1997 Jungkind
5,638,588 A 6/1997 Jungkind
5,934,599 A 8/1999 Hammerslag
6,289,558 B1 9/2001 Hammerslag
6,991,657 B1 1/2006 Price, Jr.
7,105,122 B2 9/2006 Karason
7,488,349 B2 2/2009 Einarsson
7,591,050 B2 9/2009 Hammerslag
7,950,112 B2 5/2011 Hammerslag et al.
7,954,204 B2 6/2011 Hammerslag et al.
7,992,261 B2 8/2011 Hammerslag et al.
8,091,182 B2 1/2012 Hammerslag et al.
8,157,691 B2 4/2012 Stanovskoy et al.
8,277,401 B2 10/2012 Hammerslag et al.
8,308,098 B2 11/2012 Chen
8,381,362 B2 2/2013 Hammerslag et al.
8,424,168 B2 4/2013 Soderberg et al.
8,468,657 B2 6/2013 Soderberg et al.
8,516,662 B2 8/2013 Goodman et al.
8,713,820 B2 5/2014 Kerns et al.
8,795,385 B2 8/2014 Bache
8,823,227 B2 9/2014 Bayer
8,984,719 B2 3/2015 Soderberg et al.
9,101,181 B2 8/2015 Soderberg et al.
9,113,998 B2 8/2015 Romo
9,125,455 B2 9/2015 Kerns et al.
9,138,030 B2 9/2015 Soderberg et al.
9,149,089 B2 10/2015 Cotterman et al.
9,179,729 B2 11/2015 Cotterman et al.
9,248,040 B2 2/2016 Soderberg et al.
9,259,056 B2 2/2016 Soderberg et al.
D751,281 S 3/2016 Nickel et al.
9,339,082 B2 5/2016 Hammerslag et al.
D758,061 S 6/2016 Whewell
9,375,053 B2 6/2016 Burns et al.
9,408,437 B2 8/2016 Goodman et al.
D767,269 S 9/2016 Lovett et al.
9,439,477 B2 9/2016 Neiley
9,516,923 B2 12/2016 Capra et al.
D776,421 S 1/2017 Venturini
9,532,626 B2 1/2017 Lovett et al.
9,572,705 B2 2/2017 Ingimundarson et al.
9,610,185 B2 4/2017 Capra et al.
9,629,417 B2 4/2017 Cavanagh et al.
9,681,705 B2 6/2017 Trudel et al.
9,700,101 B2 7/2017 Lovett et al.
9,706,814 B2 7/2017 Converse et al.
9,737,115 B2 8/2017 Soderberg et al.
9,743,714 B2 8/2017 Hammerslag et al.
9,763,808 B2 9/2017 Jonsson
9,770,070 B2 9/2017 Cotterman et al.
D799,810 S 10/2017 Mayberry
9,854,873 B2 1/2018 Kerns et al.
9,867,430 B2 1/2018 Hammerslag et al.
9,872,568 B2 1/2018 Capra et al.
9,872,790 B2 1/2018 Capra et al.
9,956,094 B2 5/2018 Mahon
10,004,297 B2 6/2018 Lovett
10,004,614 B1 6/2018 Johnson
10,039,348 B2 8/2018 Cavanagh et al.
10,070,695 B2 9/2018 Burns et al.
10,076,160 B2 9/2018 Burns et al.
10,100,913 B2 10/2018 Schreiber et al.
10,123,589 B2 11/2018 Soderberg et al.
D835,898 S 12/2018 Lovett
D835,976 S 12/2018 Nickel et al.
10,251,451 B2 4/2019 Converse et al.
10,267,404 B2 4/2019 Schreiber et al.
10,327,513 B2 6/2019 Soderberg et al.
10,342,294 B2 7/2019 Lovett et al.
10,362,836 B2 7/2019 Hammerslag et al.
10,406,003 B2 9/2019 Johnson
10,413,019 B2 9/2019 Soderberg et al.
10,433,999 B2 10/2019 Hammerslag et al.
10,477,922 B2 11/2019 Lovett et al.
10,492,568 B2 12/2019 Burns et al.
10,499,709 B2 12/2019 Pollack et al.
10,543,630 B2 1/2020 Hipwood et al.
10,550,924 B2 2/2020 Schmidt et al.
10,575,591 B2 3/2020 Schum et al.
10,626,973 B2 4/2020 Burger et al.
10,655,722 B2 5/2020 Dorner et al.
10,683,922 B2 6/2020 Schreiber et al.
10,702,409 B2 7/2020 Burns et al.
RE48,215 E 9/2020 Neiley
10,772,384 B2 9/2020 Whewell et al.
10,772,388 B2 9/2020 Burns et al.
D897,661 S 10/2020 Nickel
10,791,798 B2 10/2020 Lovett
10,830,328 B2 11/2020 Schreiber
10,842,230 B2 11/2020 Pollack et al.
10,849,390 B2 12/2020 Hammerslag et al.
10,863,796 B2 12/2020 Soderberg et al.
10,888,139 B2 1/2021 Burns et al.
10,918,502 B2 2/2021 Mahon
10,952,503 B2 3/2021 Trudel et al.
10,952,505 B2 3/2021 Hammerslag et al.
10,959,492 B2 3/2021 Converse et al.
D926,457 S 8/2021 Swanson
D926,458 S 8/2021 Swanson et al.
11,083,602 B2 8/2021 Mahon
11,089,837 B2 8/2021 Pollack et al.
D932,176 S 10/2021 Swanson et al.
11,220,030 B2 1/2022 Hipwood et al.
11,253,028 B2 2/2022 Lovett et al.
11,297,903 B2 4/2022 Soderberg et al.
RE49,092 E 6/2022 Neiley et al.
11,357,279 B2 6/2022 Cotterman
11,419,389 B2 8/2022 Pollack et al.
11,452,342 B2 9/2022 Hammerslag et al.
D965,257 S 10/2022 Hammerslag et al.
11,457,698 B2 10/2022 Burns et al.
11,492,228 B2 11/2022 Kruse et al.
11,504,252 B2 11/2022 Mahon
11,510,792 B2 11/2022 Mahon
D971,562 S 12/2022 Hipwood et al.
11,619,285 B2 4/2023 Bayer et al.

(56) References Cited

U.S. PATENT DOCUMENTS

| | | | | |
|---|---|---|---|---|
| 11,619,292 | B2 | 4/2023 | Schreiber et al. | |
| 11,635,132 | B2 | 4/2023 | Schmidt et al. | |
| 11,642,233 | B2 | 5/2023 | Steinberg et al. | |
| 11,674,574 | B2 | 6/2023 | Kimmelmann et al. | |
| 11,686,371 | B2 | 6/2023 | Schmidt et al. | |
| 11,730,238 | B2 | 8/2023 | Martin et al. | |
| 11,759,338 | B2 | 9/2023 | Mahon | |
| 11,806,253 | B2 | 11/2023 | Mahon et al. | |
| 11,844,667 | B2 | 12/2023 | Johnson | |
| 11,892,058 | B2 | 2/2024 | Schmidt et al. | |
| 12,000,460 | B2 | 6/2024 | Schreiber | |
| 12,225,982 | B2 | 2/2025 | Martin et al. | |
| 12,310,864 | B2 | 5/2025 | Mahon | |
| 2002/0095750 | A1 | 7/2002 | Hammerslag | |
| 2014/0257156 | A1 | 9/2014 | Capra et al. | |
| 2016/0199231 | A1 | 7/2016 | Capra | |
| 2016/0354223 | A1 | 12/2016 | Burns et al. | |
| 2018/0152076 | A1 | 5/2018 | Alei et al. | |
| 2019/0192316 | A1* | 6/2019 | Johnson | A61F 2/68 |
| 2019/0388250 | A1* | 12/2019 | Johnson | A61F 2/78 |
| 2021/0022451 | A1 | 1/2021 | Beers et al. | |
| 2021/0177098 | A1 | 6/2021 | Trudel et al. | |
| 2021/0251343 | A1 | 8/2021 | Martin et al. | |
| 2022/0175089 | A1 | 6/2022 | Pollack et al. | |
| 2023/0088406 | A1 | 3/2023 | Mahon | |
| 2023/0375083 | A1 | 11/2023 | Schreiber et al. | |
| 2024/0108481 | A1 | 4/2024 | Mahon | |
| 2024/0247685 | A1 | 7/2024 | Schreiber et al. | |
| 2024/0325173 | A1 | 10/2024 | Johnson | |
| 2024/0423317 | A1 | 12/2024 | Johnson et al. | |
| 2025/0281310 | A1 | 9/2025 | Johnson et al. | |

FOREIGN PATENT DOCUMENTS

| | | | |
|---|---|---|---|
| WO | 2014071319 | A1 | 5/2014 |
| WO | 2014074645 | A2 | 5/2014 |

OTHER PUBLICATIONS

Fitgo Quick Lacing System product information as downloaded Jan. 11, 2023; http://en.fitgotech.com/.

UTURN Smart Lacing System product information as downloaded Jan. 11, 2023; https://uturn.eu/.

* cited by examiner

FIG. 1
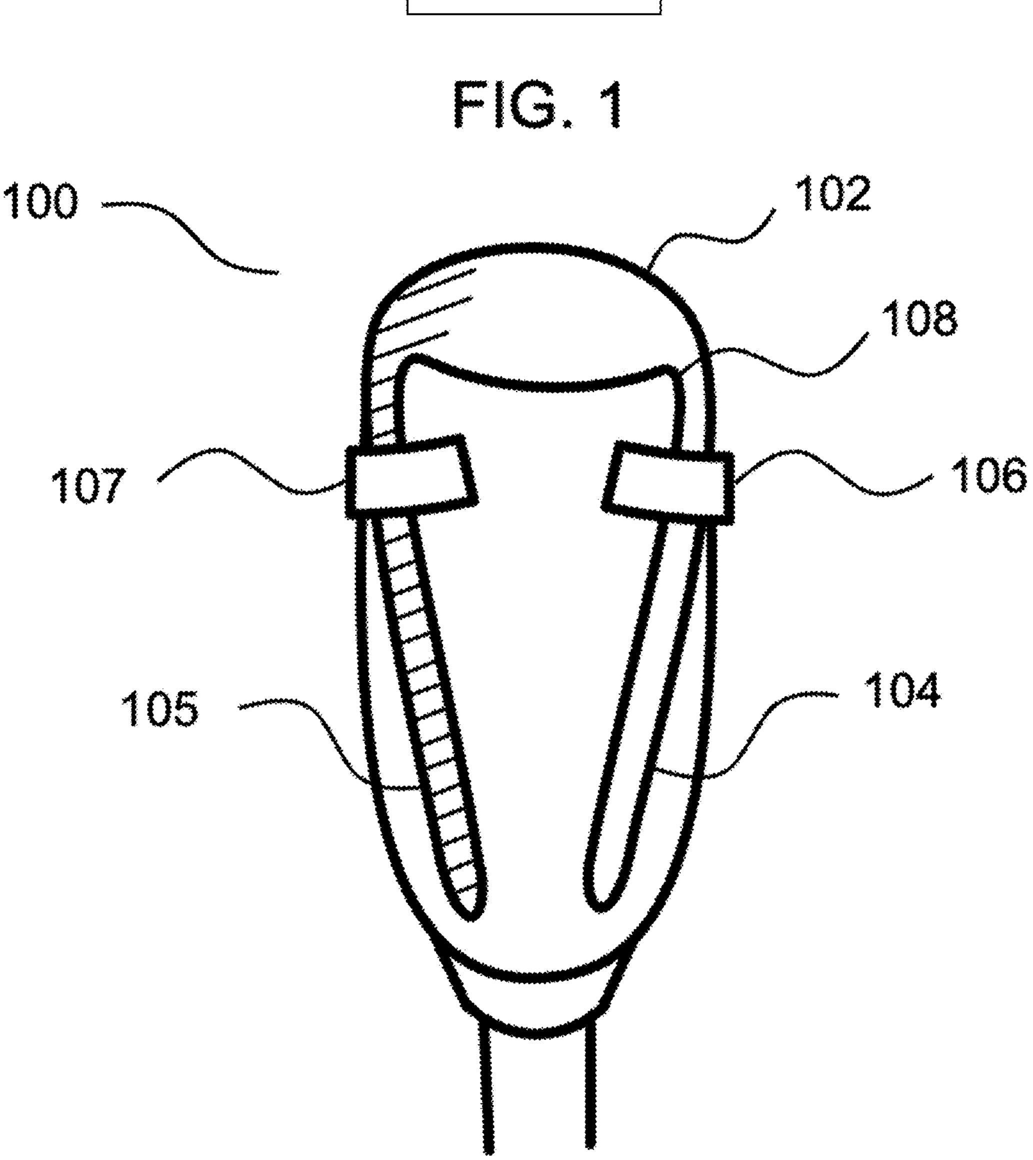

300

301

300

306
302
304

FIG. 7a
FIG. 7b
FIG. 7c
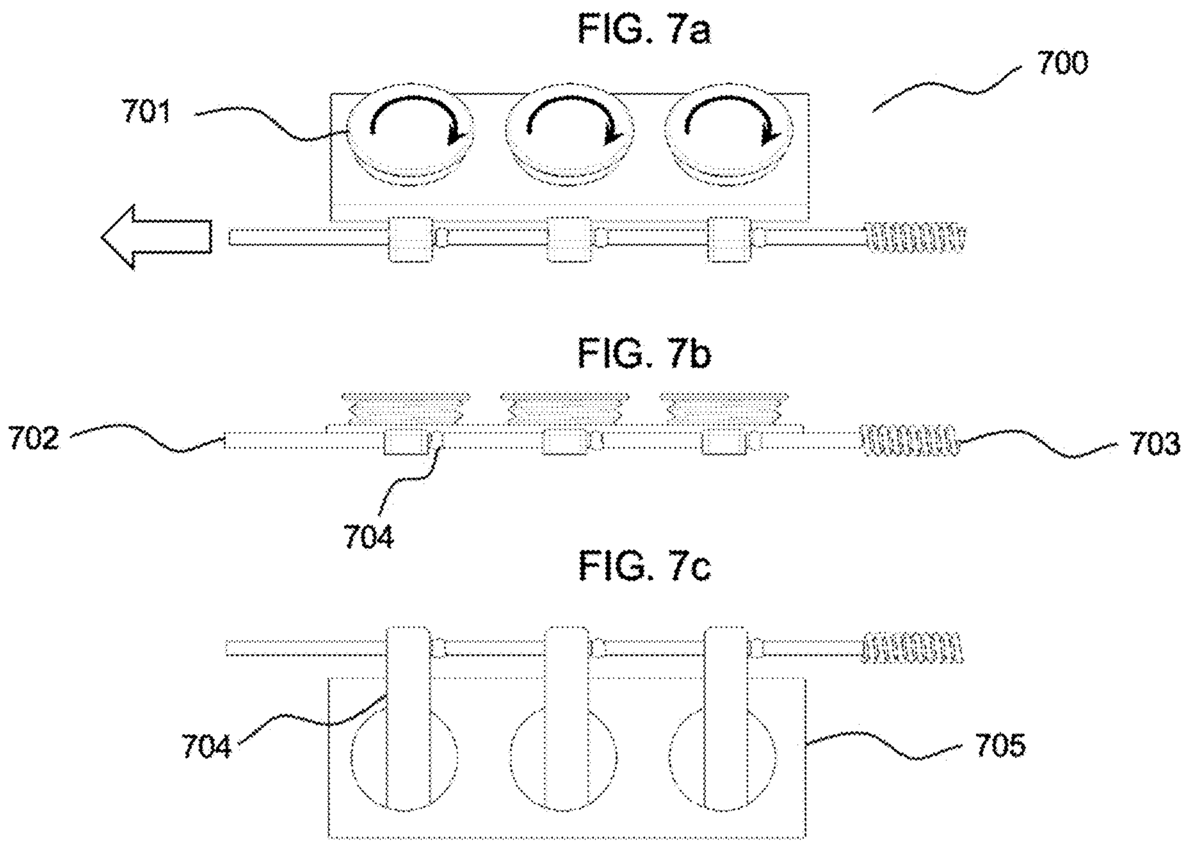
FIG. 8
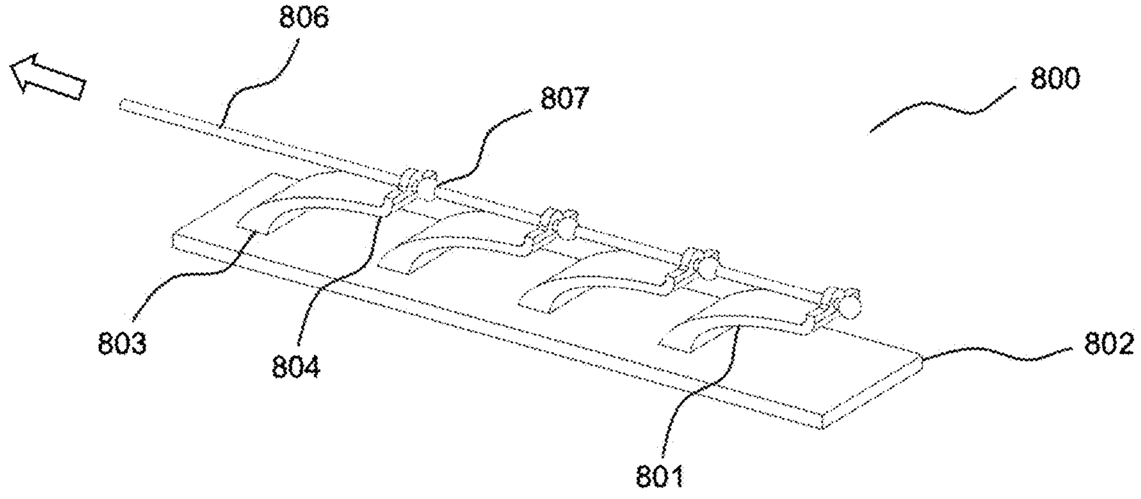

904
905
901
904
905
906

903
909
907
908

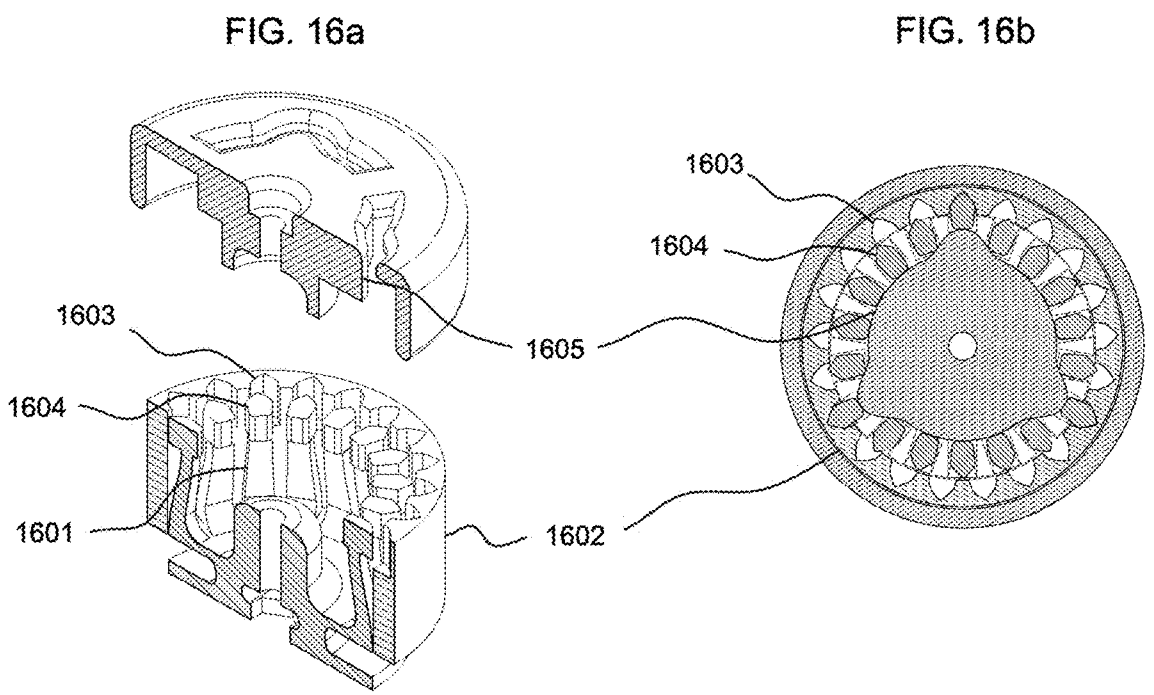
FIG. 16a
FIG. 16b
1603
1604
1605
1601
1602
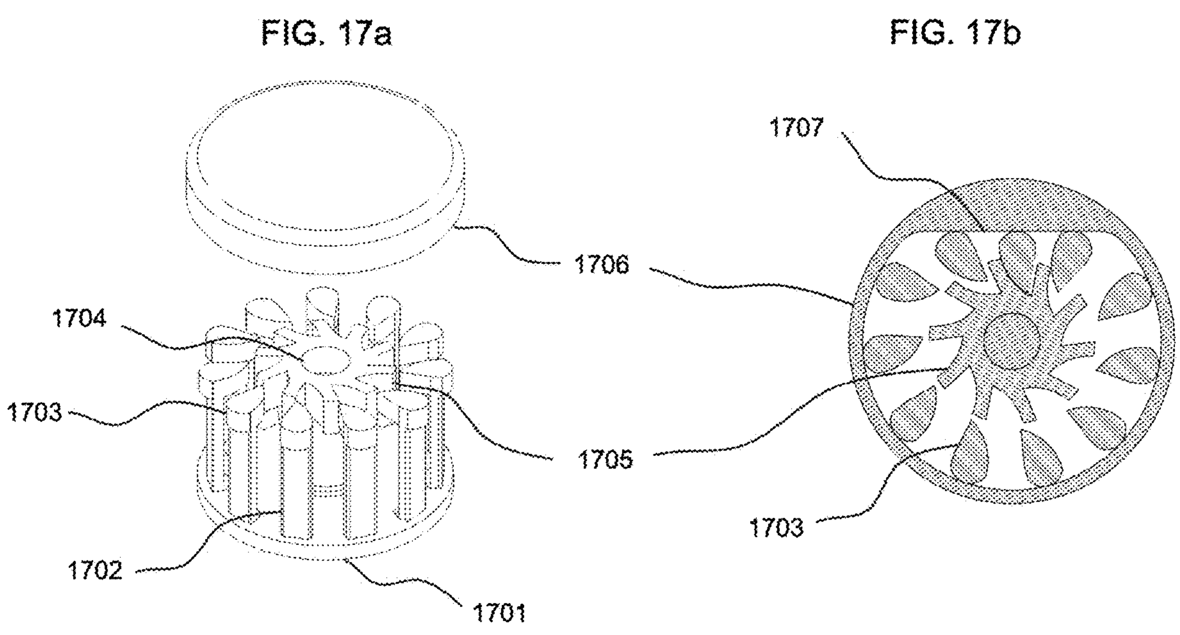
FIG. 17a
FIG. 17b
1707
1706
1704
1703
1705
1702
1701

FIG. 18a
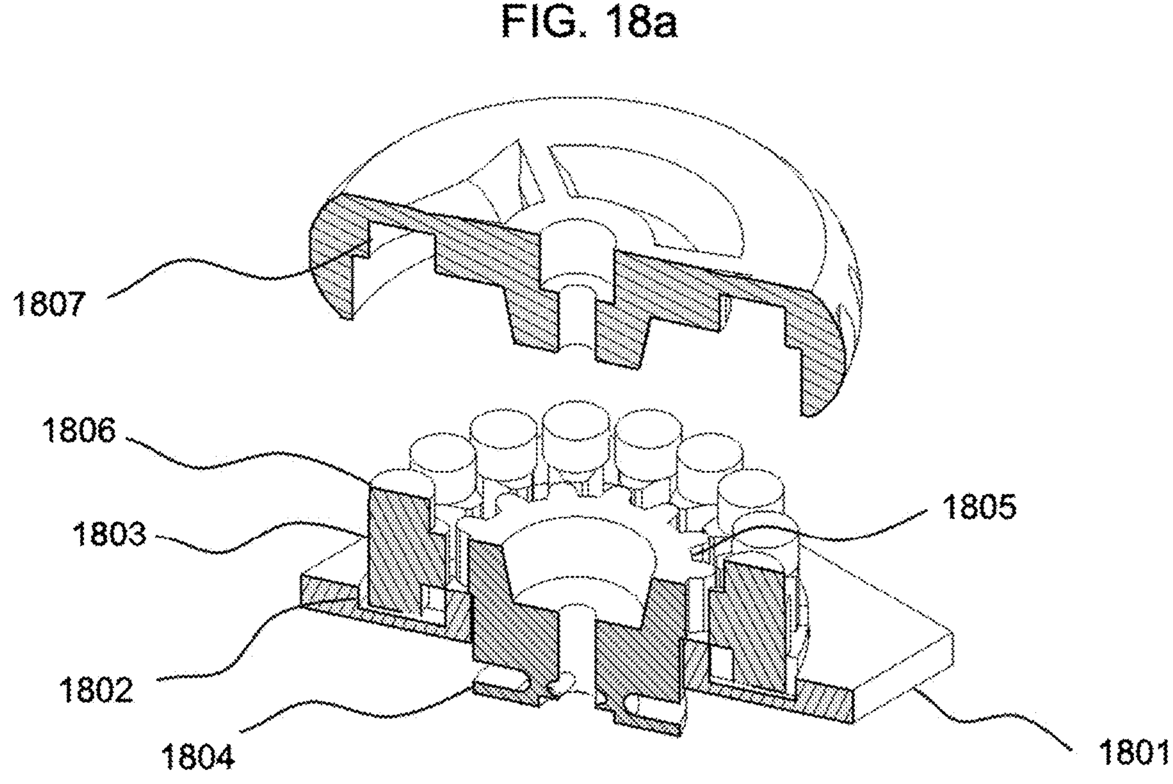
FIG. 18b
FIG. 18c
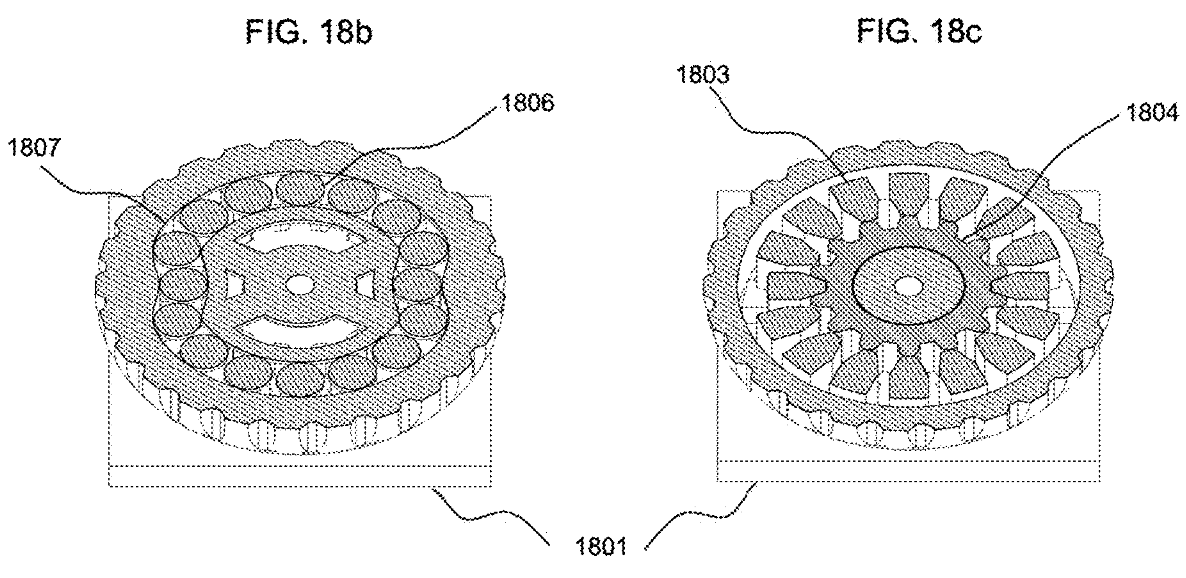

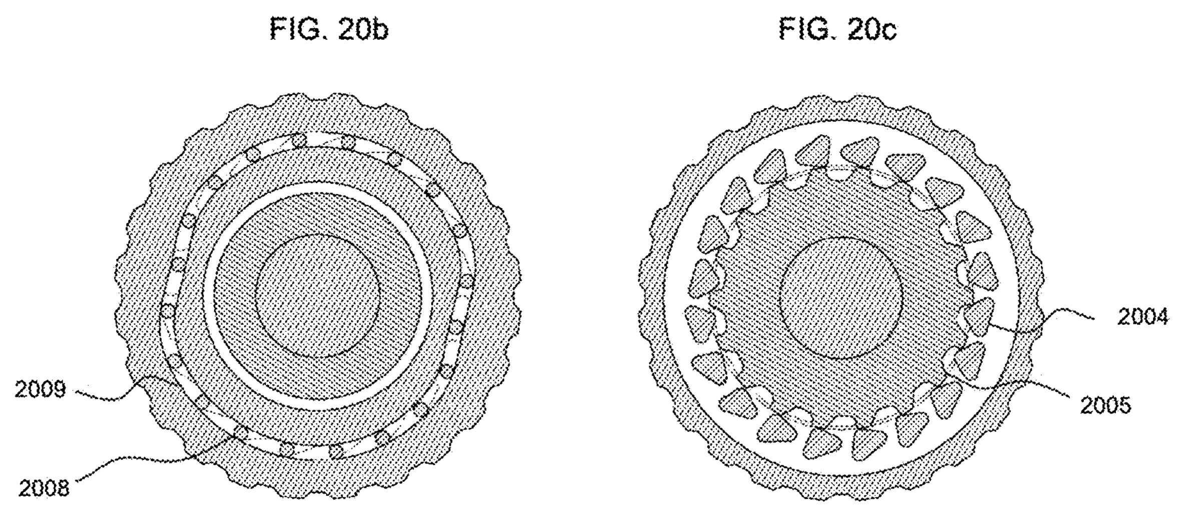
FIG. 20b
FIG. 20c
2009
2008
2004
2005
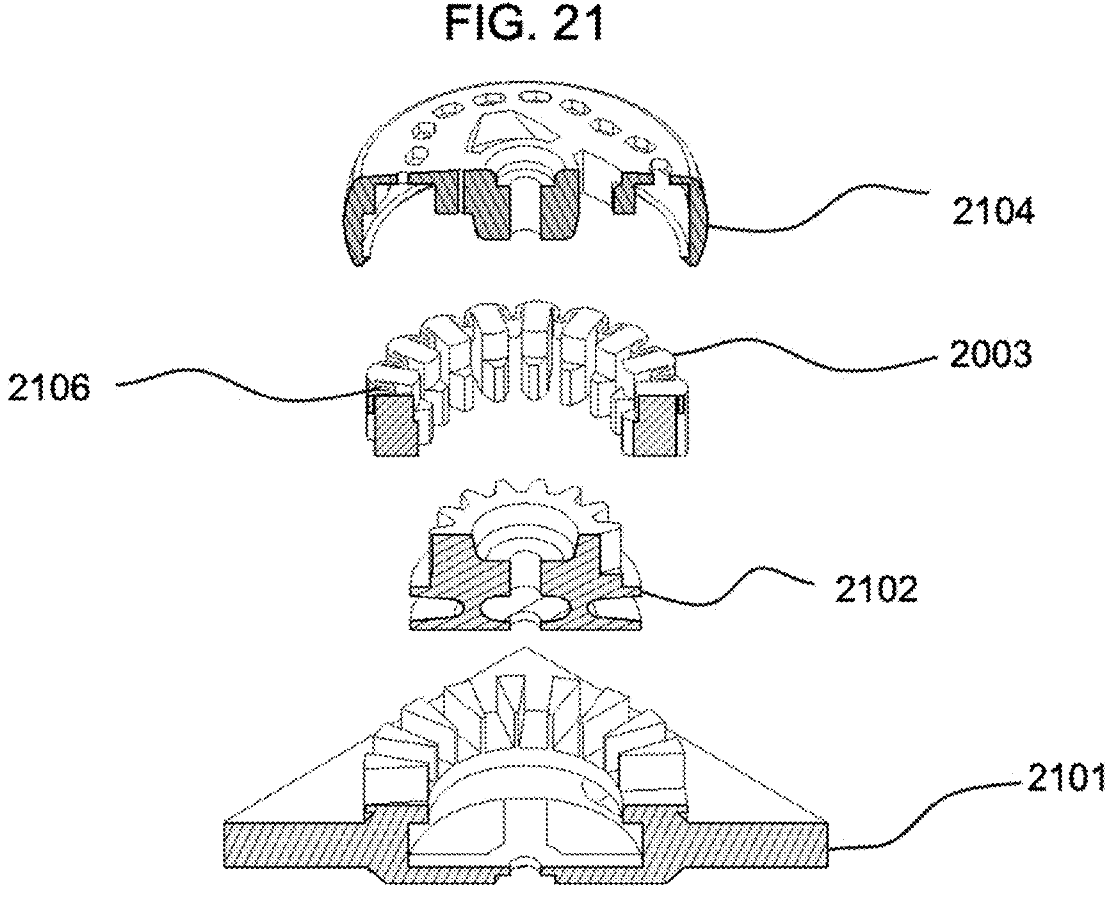
FIG. 21
2104
2003
2106
2102
2101

FIG. 24
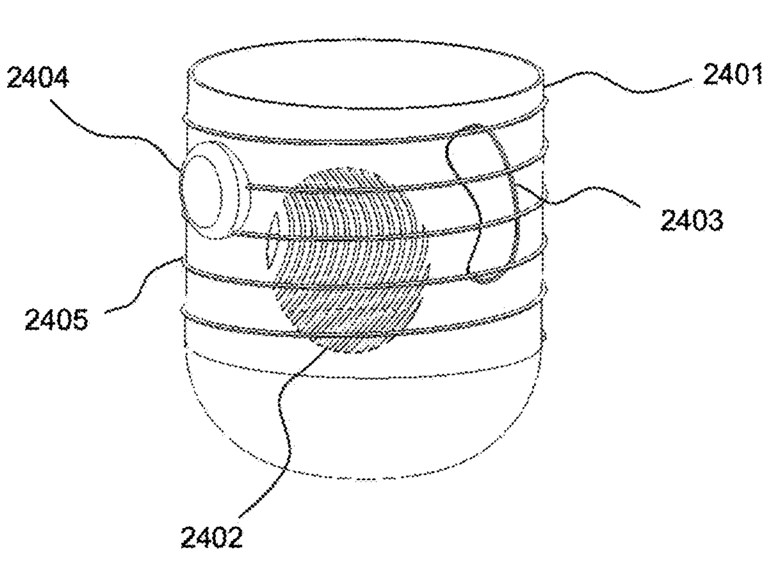
FIG. 25a
FIG. 25b
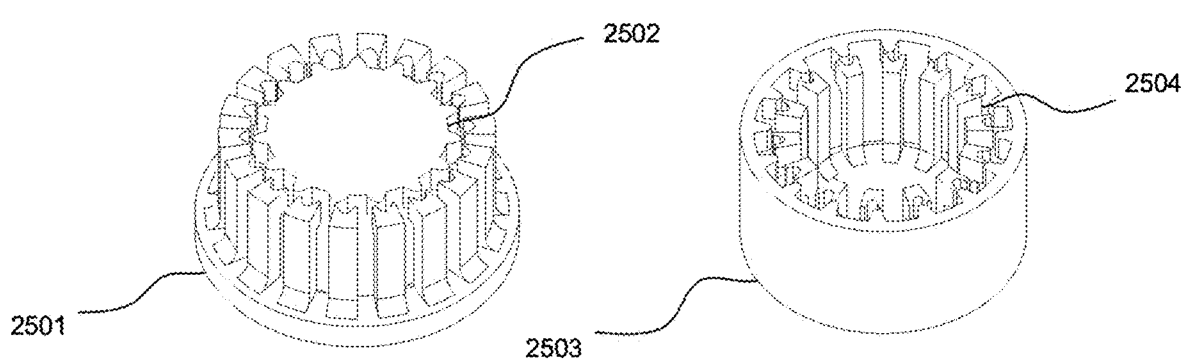

EXPANDABLE SOCKET LINER

CROSS-REFERENCES TO RELATED APPLICATIONS

The present application is a child application of and relies on the disclosures of and claims priority to and the benefit of the filing dates of the following, and the disclosures of the following applications and other applications/patents/literature cited herein are hereby incorporated by reference herein in their entirety:

U.S. patent application Ser. No. 18/387,433, filed Nov. 6, 2023,
U.S. patent application Ser. No. 18/075,203, filed Dec. 5, 2023,
U.S. patent application Ser. No. 17/902,683, filed Sep. 2, 2022,
U.S. patent application Ser. No. 17/864,675, filed Jul. 14, 2022,
U.S. patent application Ser. No. 17/700,479, filed Mar. 21, 2022,
U.S. patent application Ser. No. 17/537,476, filed Nov. 29, 2021,
U.S. patent application Ser. Nos. 17/211,590 and 17/211,635 filed Mar. 24, 2021,
U.S. patent application Ser. Nos. 17/074,571 and 17/074,542, filed Oct. 19, 2020,
U.S. patent application Ser. No. 15/585,968, filed May 3, 2017,
U.S. Provisional Patent Application No. 62/331,315 filed on May 3, 2016,
PCT Application No. PCT/US2020/047904, filed Aug. 26, 2020,
PCT Application No. PCT/US2022/021822, filed Mar. 24, 2022, and
U.S. Provisional Patent Application No. 63/394,530, filed Aug. 2, 2022.

BACKGROUND

Field of the Invention

An adjustable mechanism that transforms the rotation of a dial into a change of volume of a worn article, such as a prosthetic socket, to improve the fit of the article is described.

Description of Related Art

Achieving custom fits to body parts with a mass-produced article is difficult. Buckles, straps, zippers, elastics, Velcro, buttons, laces are all mechanical solutions that have been used with varying success.

For example, ski boots are mass produced from plastic and sized with traditional shoe sizes. Typically, ski boots come with a 'four buckle' closure where two buckles are positioned over the forefoot and two buckles are positioned above the ankle. The boot is made with overlapping "sheets" of plastic. Tightening the buckles increases the overlap, decreases the interior volume of the boot, and squeezes the boot into the foot and ankle. This system pushes the top of the foot towards the sole and causes discomfort for some.

Straps are used to secure bicycle helmets. A soft chin strap holds the helmet to the head and a hard plastic strap is used to tighten a loop to the crown of the head. Security is compromised by comfort. Tight fitting straps hold the helmet securely in place in the event of fall, but also uncomfortable to wear for long periods of time. As used herein, a worn-article can include but is not limited to, a helmet, a ski boot, a boot, a cast, an orthotic, a space suit glove, an exoskeleton, a prosthetic, a shoe, and articles that are worn on a body as would be understood by one of ordinary skill in the art.

Laces are commonly used to adjust the size of soft goods. Boxing gloves, shoes, corsets, swim trunks all use laces the same way: tightening the laces pulls two side of the article towards each other which decreases the circumference (and volume) of the article.

In the world of orthotics, straps are commonly used to provide adjustability of fit to rigid and semi-rigid articles. An orthopedic walking boot, for example, is typically constructed from a hard plastic sole plate coupled with an ankle support to prevent the wearer from flexing their ankle. Straps are used to pull the sides of the shell together squeezing the boot to the wearer's foot and calf. Buckles, ratchets, Velcro and the like are used to adjust the length of the strap (and thereby the amount of compression).

Fitting prosthetics to patients required a highly trained and skilled prosthetist. Various methods for squeezing and wedging the prosthetic socket have been developed. Even though nearly all prosthetics are bespoke, there is still a need to easily and comfortably adjust the volume of the socket since a person's limb will change in size and shape as the limb heals and finally over the course of the day and from week to week (just as the size of a person's foot changes over the course of a day).

U.S. Pat. No. 11,759,338 assigned to Click Holdings, LLC describes an adjustable prosthetic socket with a panel that is attached by a hinge to the socket receptacle. A tension line follows a guide path such that applying tension squeezes the panel radially towards the interior of the receptacle decreasing the volume of the interior of the receptacle.

U.S. Pat. No. 11,083,602 assigned to Click Holdings, LLC describes an adjustable prosthetic socket with a plurality of ports and free-floating panels. A first tension line follows a first guide path and couples with a subset of the panels; a second tension line follows a second guide path and couples with the remainder of the panels. Applying tension to the first tension line draws the subset of panels radially towards the center of the receptacle in the first zone whereas applying tension to the second tension line draws the remainder of the panels radially towards the center of the receptacle. In this manner, the interior volume of the receptacle can be decreased independently in different regions.

U.S. Pat. No. 7,950,112 assigned to BOA Technology, Inc describes a reel-based closure lacing system for shoes with three lacing zones and two tensioning devices. The first and second lacing zones on disposed on the forefoot. The third lacing zone wraps the ankle. The tensioning devices are independent and control the tension of the laces in the first and second lacing zones. The third lacing zone is controlled by the tighter of the first or second lacing zones. All three lacing zones work by drawing the sides of the shoe towards each other thereby decreasing the volume of the interior of the shoe.

U.S. Pat. No. 9,872,790 assigned to BOA Technology, Inc describes a lacing system to apply an inwards radial pressure to a limb inside a prosthetic socket. A slidable element is configured on a port or panel on the socket wherein a lace runs over or through it. By altering the position of the slidable element, the lever arm coupling the tension force of the lace to the port or panel can be increased or decreased thereby adjusting the inwards force of the port or panel on the limb as the port or panel displaces inwards.

Unlike the solutions described above, the invention disclosed herein thickens a conformable pad disposed between the exterior shell and the body part by converting a tension—as applied by an adjustable tensioning mechanism, such as a dial—into an expansion action of the pad. The dial generates a mechanical advantage with a unique drive system thereby making it easy for the wearer to use and has the ability to incrementally increase or decrease the applied tension to fine tune the fit.

There are four common types of drive systems known in the art that are used to provide mechanical advantage and increase torque. The simplest is a gear drivetrain which consists of two or more gears (typically spur gears) where a small gear drives a larger gear (the driven gear).

A planetary gear drive is slightly more complex and uses a sun gear to drive several planetary gears mounted to a carriage around an internal ring gear. The configuration generates more torque than that applied to drive the sun gear.

A cycloidal gear drive consists of an eccentric drive shaft that drives a cycloidal disc around pins. The output shaft is driven by the cycloidal disc.

Finally, a harmonic drive consists of a circular spline, a flex spline, and a wave generator. The inner flex spline typically has two fewer levers than the circular spline. The mechanical advantage for a traditional harmonic drive with an elliptical wave generator is given by the following ratio:

NFS/2:1 where NFS=the number of levers on the flex spline

For example, the mechanical advantage of a harmonic drive whose flex spline had 200 levers would be 100:1.

The various types of drive trains have their own advantages and disadvantages. Planetary gears drives are simple to manufacture but they can be back-driven. Harmonic drives have zero backlash but they are not applicable for low mechanical advantage applications (e.g., <30:1).

SUMMARY OF THE INVENTION

Fitting garments, devices, accessories to body parts can be difficult especially if the article to be fitted is rigid or semi-rigid. Consider, for example, fitting a ski boot to a foot.

The function of a ski boot is to connect the wearer securely to the ski. Any slop or give in the fit of the foot in the ski boot is a loss of feedback and control of the ski. Ski racing boots typically use cork as the cushion between the ski boot and the racer's foot because cork is so stiff. Ski racers are willing to trade comfort for control.

The human foot is wider at the ankle joint than at the ankle immediately above it. Putting a foot into a hard shell such as a ski boot means that either the opening needs to be wide enough to accept the ankle joint or the shell needs to separate into pieces to allow the foot to enter. Most modern ski boots opt for the former method which necessitates the ability to tighten the cuff around the ankle (at a minimum) to achieve the desired foot/boot/ski feedback.

The bodies of vertebrates simply do not taper continuously and gradually from their cores to their limbs. Putting a ski boot on a person or a saddle on a horse or goggles on a greyhound requires a means to tighten the article to secure it. Traditional buckles, straps, laces, zippers and the like are often sufficient for soft goods such as clothing. When the article to be fitted has a hard shell a compromise between a secure fit and comfort is often needed.

The below-the-knee prosthetic (100) shown in FIG. 1, which is an example of existing art, is an example of an article to be worn that has a hard shell. The socket (102) is typically custom made of a rigid or semi-rigid material such as a fiberglass laminate. A liner (not shown) is fitted between the residual limb and the interior of the socket. Sockets are custom made because the size and shape of everyone's residual limb is unique and to function properly they need to be secure (to transmit the forces from standing, walking, and climbing stairs from the foot blade to the wearer's leg. The wearer has some control over fit adjustment of the prosthetic (100) due to the slits (104, 105) in the socket which creates a hinged panel (108). Tightening the buckles (106, 107) pulls the panel (108) radially towards the interior of the socket.

The present invention is superior to existing art because it allows a gentle yet secure compression of the limb by expanding a pad, strap, or area between the limb and the inner socket wall. In addition, the expandable article of the present invention can either be built into the device at time of manufacture or installed into an existing device after fabrication. The expandable article of the present invention is also superior to existing art because, in aspects, it does not require cuts, ports, slits, and the like to be made in the hard shell which reduce the structural integrity of the prosthetic. Unlike traditional pads and spacers, the expandable article of the present invention is easily adjustable by the wearer while the prosthetic is worn.

DESCRIPTION OF THE FIGURES

The accompanying drawings illustrate certain aspects of some of the embodiments of the present invention and should not be used to limit or define the invention. Together with the written description the drawings serve to explain certain principles of the invention.

FIG. 1 is a frontal view of a below the knee prosthetic device.

FIGS. 7*a*-7*c* illustrate a screw variant of the invention.

FIG. 8 illustrates a flexible lever arm variant of the invention.

FIGS. 16*a* and 16*b* show a trilobe wave generator variant of a flexible lever PhIL harmonic drive.

FIGS. 17*a* and 17*b* show a flexible lever with an asymmetric tooth profile suitable for a PhIL harmonic drive.

FIGS. 18*a*-18*c* shows a sliding lever variant of a PhIL harmonic drive.

FIGS. 20*a-c* shows a rotating lever variant of a PhIL harmonic drive.

FIG. 21 shows a variant of a PhIL harmonic drive where the slidable levers are connected by a flexible element.

FIG. 24 is an orthogonal view of a prosthetic with regions of varying compliance.

FIGS. 25*a* and 25*b* are illustrations of variants of PhIL harmonic drives with the levers configured to flex radially inwards and to flex radially outwards.

DETAILED DESCRIPTION OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

Figure 2:
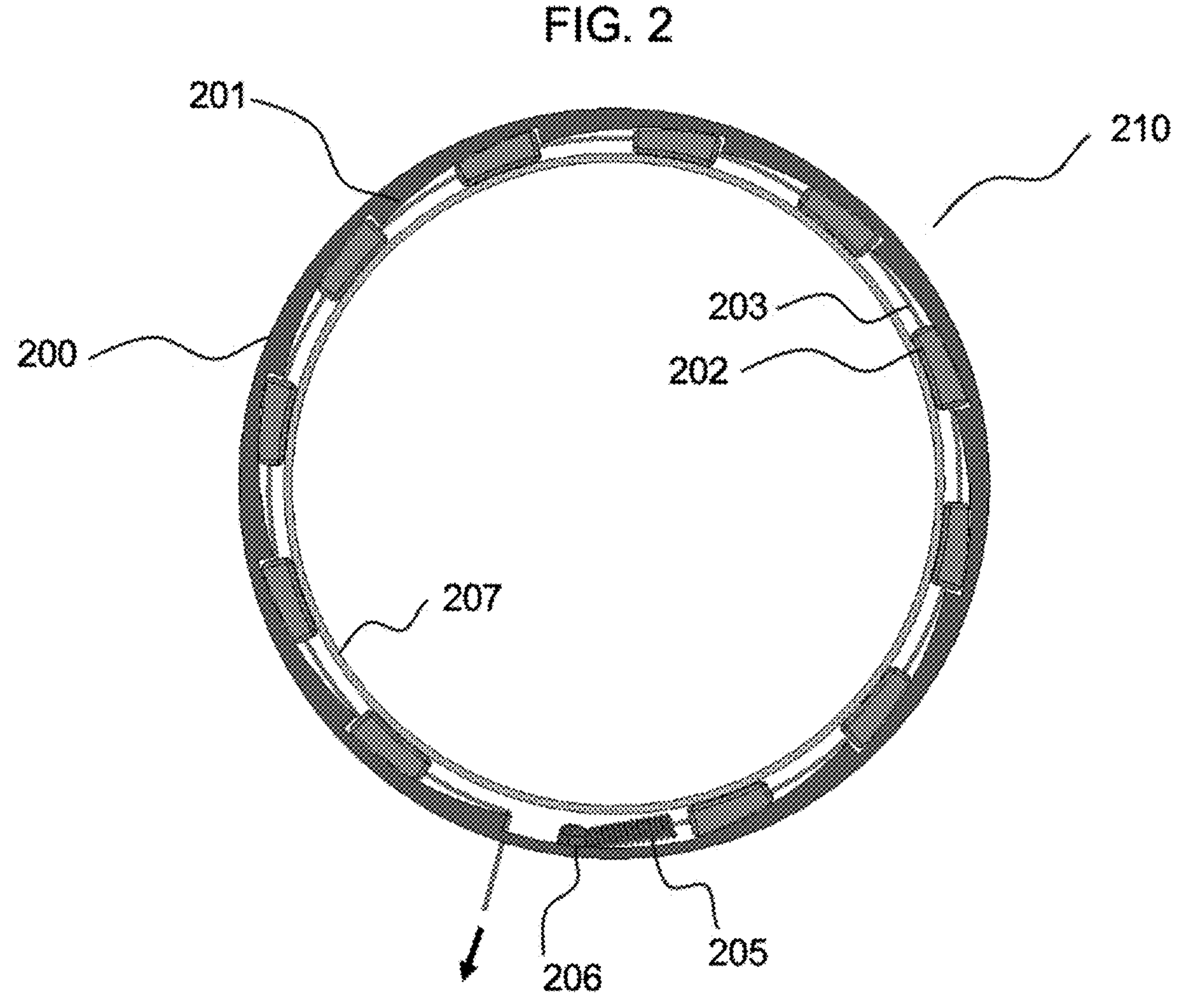
FIG. 2 is a top view of connected series of wedges in a prosthetic socket.

FIG. 2 shows a top view of one aspect of the present invention configured to be fabricated into a prosthetic (210). Ramps or inclines (201) are disposed along the inner circumference of the socket (200). A plurality of wedges (202) are connected by a tensile element (203). One end of the tensile element is connected to an elastic element (205) which is anchored to the socket (206). The other end of the tensile element passes through a small hole in the socket wall where it is coupled with a tension adjustment mechanism (not shown). When a force is applied by the tension adjustment mechanism in the direction shown by the arrow, the plurality of wedges slide along the ramps and apply radial pressure to the liner (207).

As configured in FIG. 2 the radial pressure is substantially the same circumferentially around the limb (not shown) inside the socket. By altering the size of the ramps/wedges, the angle of the incline, the spacing of the ramps/wedges, or combinations thereof the radial pressure can be modified so that it is different from one position to another circumferentially. In this manner, the applied radial pressure can be tailored to avoid a sensitive area or wound on the residual limb. (Or, in the case of an article such as a ski boot, the ankle bone.)

When the force applied by the adjustable tensioning mechanism is reduced, the elastic element (205) draws the wedges backwards along the ramps reducing the radial pressure. The elastic element can be a spring, a piston, a TPU band, rubber, an elastic material, or the like. In other aspects multiple elastic elements could be employed (for example, between every third wedge element). In other aspects, the tensile elements or the wedge elements could serve as the elastic element or contribute to the elastic recovery forces, or combinations thereof.

In other aspects the ramps or inclines may be part of a piece that is not integral with the socket but affixed to it at a later time. An assembly comprising a flexible band of ramps, wedges connected by tensile elements, an elastic element, and a flexible liner could be retrofitted into an existing article and connected to an adjustable tensioning mechanism.

The adjustable tensioning mechanism can be a dial, a lever, a ratchet, a strap or the like. Preferably, the adjustable tensioning mechanism has a mechanical advantage such that the force to turn the dial (or flip the lever, etc.) is less than the force applied to the tensile element.

Figures 3A, 3B:
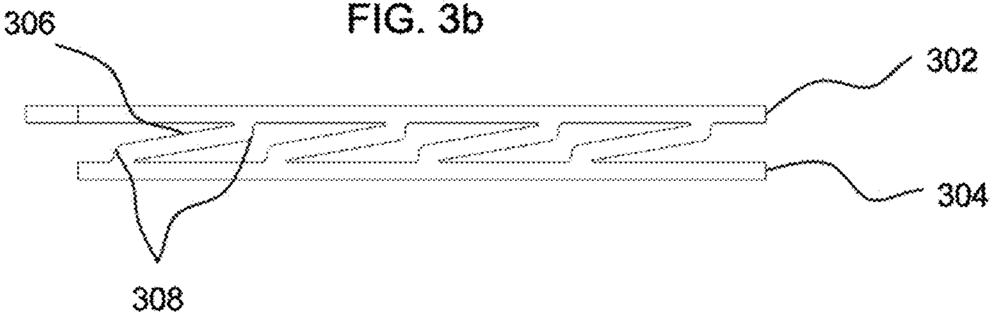
FIGS. 3*a* and 3*b* illustrate a 4-bar linkage variant of the invention.
Figures 4A, 4B:
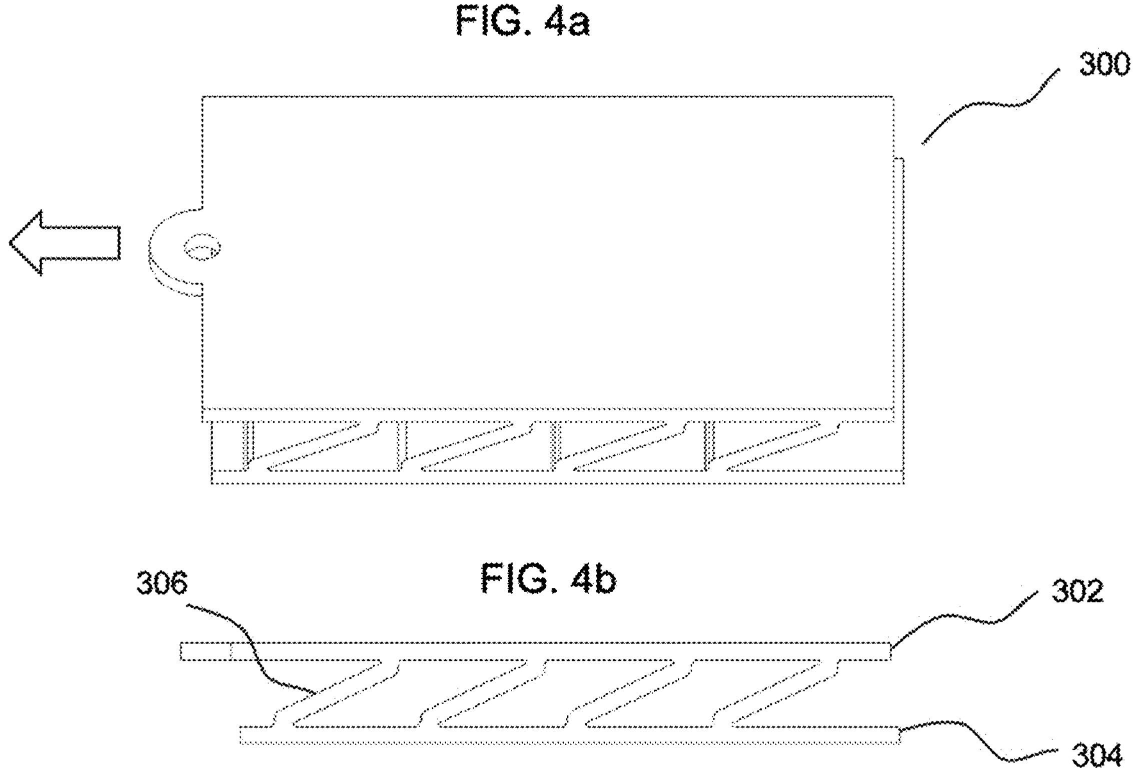
FIGS. 4*a* and 4*b* illustrate the effect of applying a tension to the 4-bar linkage variant shown in FIGS. 3*a* and 3*b*.

FIG. 3*a* shows an orthogonal view of another aspect of the present invention in the form of a pad (300). FIG. 3*b* shows a side view of the pad which has a top layer (302) and a bottom layer (304) that are connected by a plurality of linkages (306). The linkages are connected by hinge points (308) to the top and bottom layers. A fastening point (301) for a tensile element (not shown) is provided. In FIG. 4*a* the arrow shows the direction of force applied by the tensile element. As a result of the force, the top layer (302) lifts up and to the left of the bottom layer (304). In this manner, applying a tensioning force expands the thickness of the pad (300).

The pad shown in FIGS. 3 and 4, could be extruded, cast, injection molded, or the like out of a single material as a unitary object. The hinge points (308) are commonly known as 'living hinges'. The living hinges are preferably designed such that when the force is released the hinges pull the top and bottom layers back to their original positions.

In another aspect, the pad could be fabricated in the expanded position. In this case, applying a force to the top layer in the opposite direction as shown in FIG. 4*a* would compress the article. That is, an adjustable tensioning mechanism could be used to apply a force to the tensile element to collapse the expandable pad before the device is donned. Releasing some or all of the tension would cause the expandable pad to relax to its expanded state. This would be a way to ensure that the wearer could not over tighten the fit.

In another aspect, traditional hinges or pivot points could also be employed in which case an elastic element could be added to pull the top and bottom layers back to their original positions.

The final shape of the article could be cut, punched, or stamped from a sheet (for example an oval or round rectangle) to be used as an expandable condyle pad for a knee orthotic.

In another aspect, one or more materials could be used to make the unitary article shown in FIGS. 3 and 4. As a non-limiting example, the top and bottom layers may be formed from a low durometer TPU while the linkages may be formed from a higher durometer TPU via co-extrusion.

A foam cutout, silicone pad, fabric piece, or the like could be affixed to the top layer (302) to help distribute the forces applied by the expandable pad. In another aspect, features (such as flexible ribs, flexible columns, thin arches, a foamed layer, and the like) could be molded, cast, or extruded on the upper surface of the top layer to build in a soft layer as part of the unitary article.

Selecting the right material (or materials) for a unitary design could make the article naturally waterproof or sweat resistant. With the correct materials and/or post processing the tensile element could be part of the unitary design. For example, if top and bottom layers were made from polyethylene, drawing tabs extending from the top and bottom layers could induce necking transforming the tabs into laces. Alternatively, embossing long tabs with a pattern and punching holes could increase their flexibility and would allow them to be fixed on posts elsewhere on the device. These methods would enable a very low cost expandable pad or strap which would be beneficial for instances where the pad or strap needs to be disposable—for example, if the pad is used inside a tubelike article to immobilize a broken limb for a field expedient cast.

The invention of FIGS. 3 and 4 imparts an expansion force as well as a translational force between the top and bottom layers. If no translation is desired, a slidable pad or element may be affixed to the top layer. In some instances, translation may be very desirable to help fight migration of the device (unwanted slippage of the device with respect to the body part it covers.) By orienting the direction of translation opposite of the expected migration direction, the act of expanding the pad or strap to adjust the fit would also counter some of the migration forces. In these situations, a non-slip surface on the top layer (or padding connected to the top layer) would be advantageous.

Figure 5A:
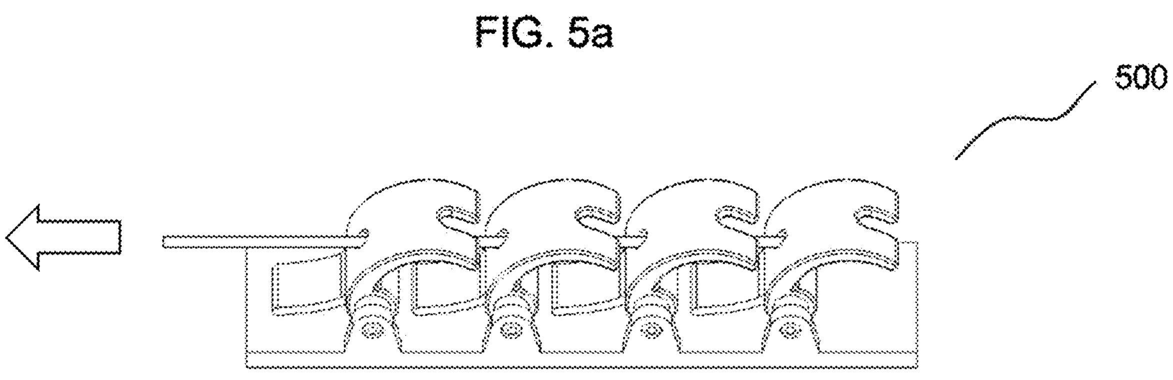
FIGS. 5*a* and 5*b* illustrate a lever arm variant of the invention.
Figure 5B:
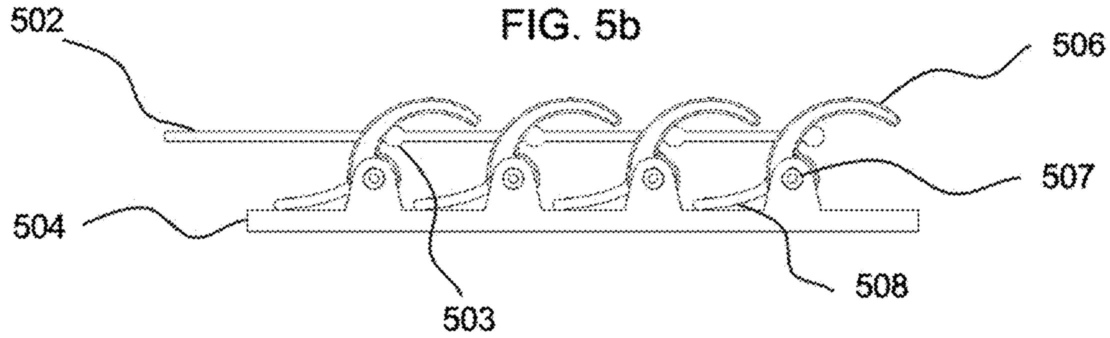

FIG. 5*a* shows another aspect of the invention (500) that has a plurality of connected lever arms. FIG. 5*b* is a side view of the assembly. The base (504) has plurality of hinge mounts (507) in which lifters (506) can rotate. A tensile element (502) threads through the lifters and a knot, swelling, crimp, or the like (503) prevents the tensile element from sliding through the lifter. The lifters have a tail (508) which acts as a spring. When a force is applied to the tensile element via an adjustable tensioning mechanism (not shown), the lifters pivot about the hinge mounts and flex the tails. When the force to the tensile element is released, the tails return to their unflexed position which rotates the lifters downwards.

The upper surface of the lifters may be flexible and conformable to apply the expansion force directly to the wearer. Alternatively, a pad, foam cutout, fabric piece, gel pad, or the like may be positioned on top of the array of lifters to distribute the force.

In another aspect, an elastic element may be placed in line with the tensile element at the end opposite of the adjustable tensioning mechanism to help draw the lifters back down and return to the downwards position. The additional elastic element may supplement the spring action of the tails or replace them. In another aspect, the tensile element may be elastic throughout its length or a portion of its length for the purpose of restoring the lifters to their downward position.

In another aspect, the lifters are cam shaped with a varying radius as measured from the axis of rotation and substantially inflexible.

Figure 6A:
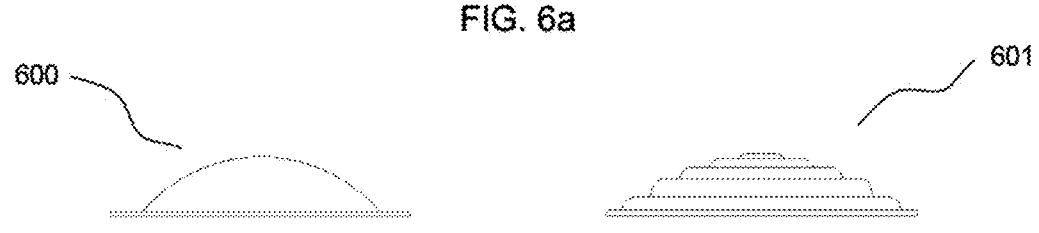
FIGS. 6*a* and 6*b* illustrate a dome and multi-position dome variant of the invention.
Figure 6B:
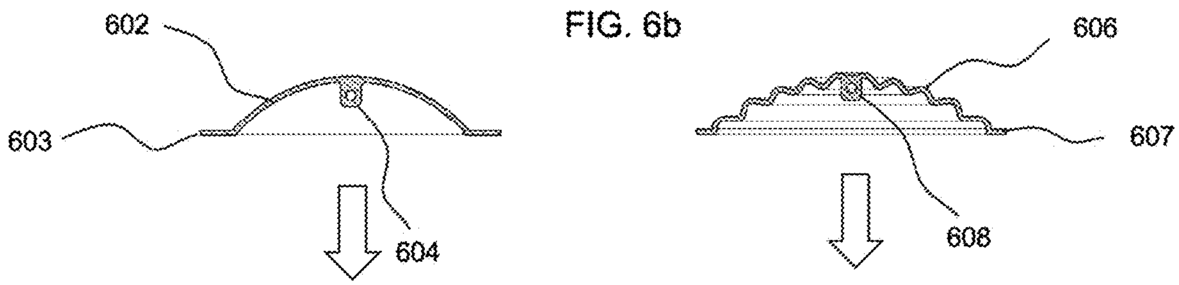

FIG. 6*a* shows a side view of another aspect of the invention. A smooth dome (600) and a stepped dome (601) are illustrated. FIG. 6*b* shows a cut-away view of the smooth dome and stepped dome. The smooth dome is bi-stable; that is, it has two stable configurations, dome rounded up and dome rounded down.

The smooth dome has a flange (603) which is affixed to the inner surface of the shell of the worn device which is being fitted with an expandable pad or strap. A tensile element (not shown) is coupled with a center anchor (604). When a force is applied to the tensile element in the direction of the arrow, the top surface of the dome (602) collapses downwards into its other stable configuration. The multi-position dome also has a flange (607) which is affixed to the inner surface of the shell of the worn device. A tensile element (not shown) is coupled with a center anchor (608). When a force is applied to the tensile element in the direction of the arrow, the top surface (606) of the multi-position dome collapses downwards. The stepped dome has several stable configurations.

This aspect of the invention is expanded in the low tension state and collapses in the high tension state. This may be particularly useful for body parts with a natural concavity such as the arch of a foot. The shapes illustrated in FIG. 6*a* could be used singly or ganged together to cover a larger area. One skilled in the art could envision other shapes that act in a similar manner.

FIG. 7*a* shows an orthogonal view another aspect of the present invention (700) which utilizes a plurality of screw elements (701). FIG. 7*b* is a side view showing the tensile element (702) coupled to each of the screw elements and affixed to an elastic element (703). Knots, crimps, and the like (704) couple the motion of the tensile element to each screw element. FIG. 7*c* is a bottom view showing the connection of the lever arms (704) to the screw elements. The screw elements are housed in a base (705).

Applying a force to the tensile element via the tension adjustment mechanism (not shown) causes the plurality of screw elements to rotate as shown by the curved arrows in FIG. 7*a*. This rotation lifts the screw elements raising their top surface away from the base. a pad, foam cutout, fabric piece, gel pad, or the like positioned on tops of the screw elements would expand upwards away from the base and create a compressive force between the interior of the shell of the device and the limb. Relaxing the force allows the spring element to return the screw elements to their downward position thereby collapsing the expandable pad or strap.

FIG. 8 shows an orthogonal view of another aspect of the present invention (800) in the form of a strap. A plurality of levers (801) are attached to a base (802). The levers have a bottom (803) and a top (804) where the bottom is attached or integral with the base. A hole or other connection means is placed at the top. A tensile element (806) is threaded through the connection means and stops (807) prevents the tensile element from gliding freely through the connection means. The stop can be a knot, a swelling, crimp, an attachment, or the like.

When a force is applied by an adjustable tensioning mechanism (not shown) in the direction of the arrow is applied to the tensile element, the levers flex upwards increasing the distance from the tops to the base thereby expanding the thickness of the strap. The inherent elasticity of the levers draws them downwards when the force on the tensile element is reduced. If additional return force is needed and additional elastic element (not shown) may be affixed at the end of the tensile element opposite of the adjustable tensioning mechanism.

A pad, foam cutout, fabric piece, gel pad, or the like may be positioned on tops of levers if needed to provide softness.

Figures 9A, 9B, 9C:
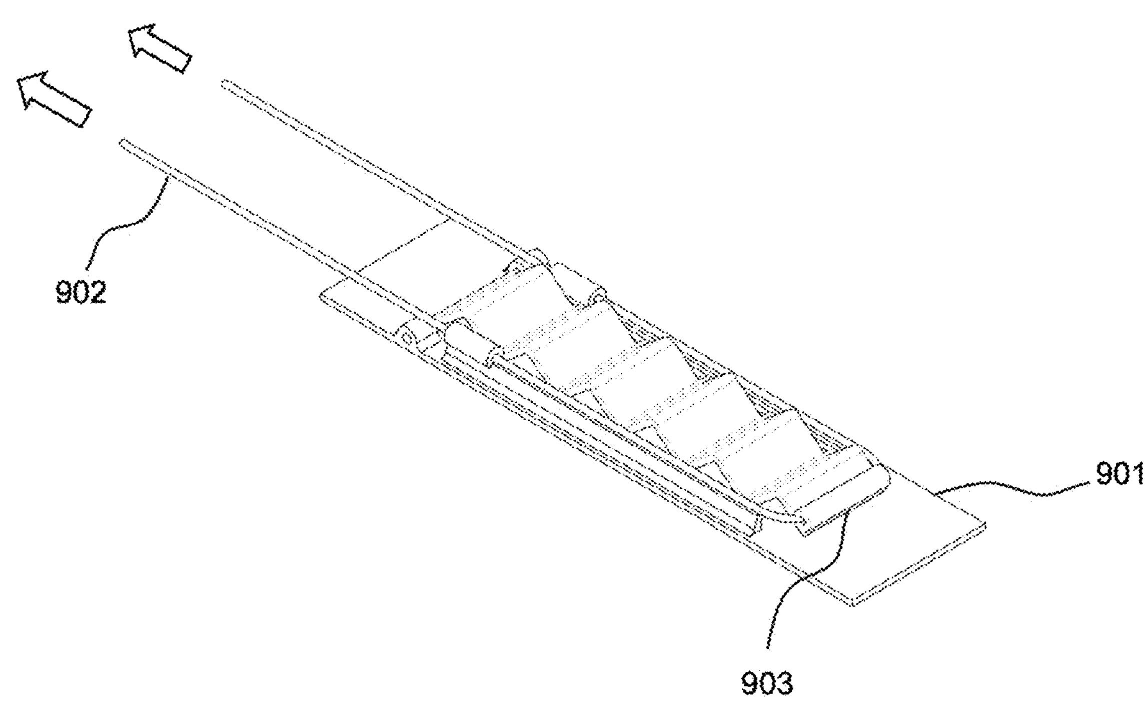
FIGS. 9*a*-9*c* illustrate an orthotic view of an accordion variant.

FIG. 9*a* shows an orthogonal view of another aspect of the present invention with three components: a base (901), a tensile element (902), and an accordion-like element (903). Applying a force on the ends of the tensile element in the direction shown by the arrows collapses the accordion-like element raising the tops of the folds (909) higher above the surface of the base.

FIG. 9*b* shows just the base component (901). Guide paths for the tensile element (905) are provided on either side of the base on the tops of rails (906). Two pivot points (904) are positioned at the ends of the rails. FIG. 9*c* shows just the accordion-like component (903). A pin (907) is positioned at a first end of the component that fits in the holes of the pivot points (904) on the base. The pin and hole combination keeps the first end of the accordion-like element (903) from translating with respect to the base while allowing it to rotate. A plurality of protrusions (908) are positioned at the bottoms of the folds of the accordion-like element. These protrusions fit under the overhangs of the rails (906) on the base. The protrusions and rails combination allow the accordion-like element to translate along the plane of the base but prevents the entire accordion-like element from lifting from the base.

When a force is applied to the tensile element that is secured to the second end of the accordion-like element, the accordion-like element is compressed and folds upon itself thus lifting the tops of the folds (909) higher above the surface of the base. In some aspects, the accordion-like element (903) is made from a material which acts as a spring drawing the assembly flat when the applied force is released. In some aspects, an additional elastic element is positioned between the second end of the accordion-like element and the base to draw the accordion-like element flatter when the applied force is released.

Figure 10:
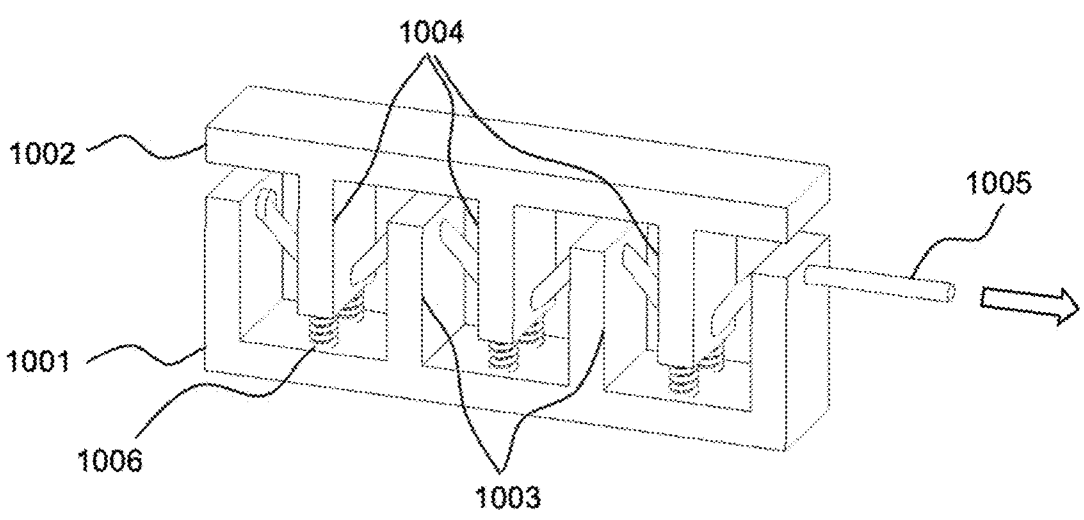
FIG. 10 is an orthogonal view of an interlaced digit variant.

FIG. 10 is a side view of another aspect of the present invention. A bottom element (1001) and a top element (1002) have a plurality of lever-like protrusions (1003) and (1004) respectively. A tensile element (1005) zig-zags between the ends of the protrusions as shown. When an adjustable tensioning mechanism (not shown) applies a force to the tensile element in the direction shown by the arrow, a lifting force separates the top element from the bottom element. Elastic elements (1006) connect the bottom element to the top element. When the top element lifts away from the bottom element, the elastic elements are stretched. When the force on the tensile element is released, the elastic elements retract the top element back towards the bottom element.

Figure 11:
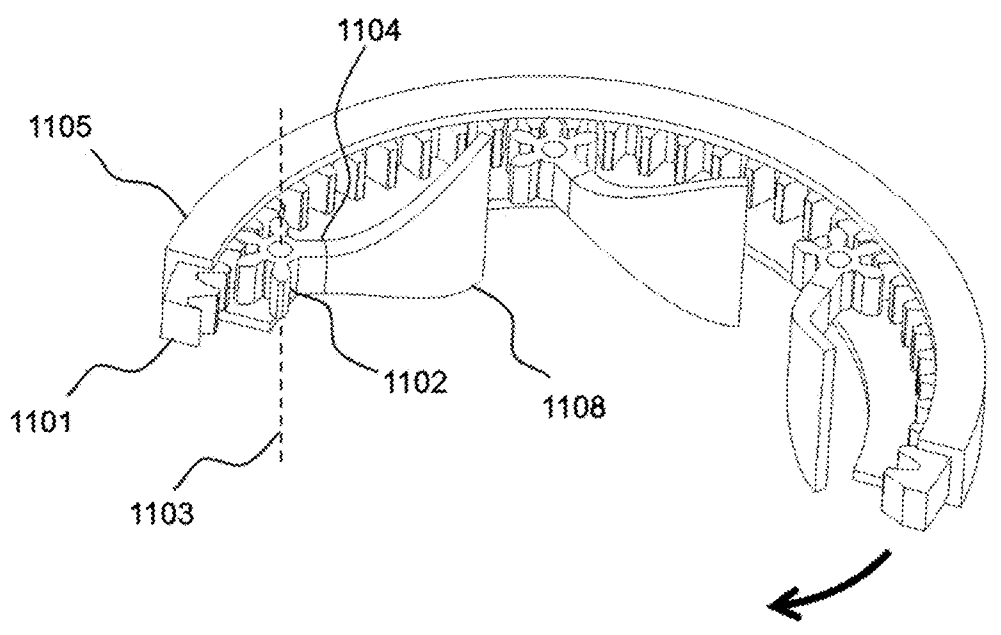
FIG. 11 is an orthogonal view of a ring gear driven variant.

FIG. 11 is an orthogonal view of another aspect of the present invention. A ring gear (1101) is positioned on the periphery of the expansion mechanism in a track (1105) A plurality of vanes (1104) comprising a toothed gear (1102) with a pivot point (1103) are positioned around the ring gear. When a force is applied to a tensile element (not shown) in the direction of the arrow, the ring gear slides in the track. The teeth of the ring gear engage with the teeth of the vanes causing the vanes to rotate about their pivot points. The flats of the vanes (1108) expand away from the outer walls of the socket filling space.

Figure 22:
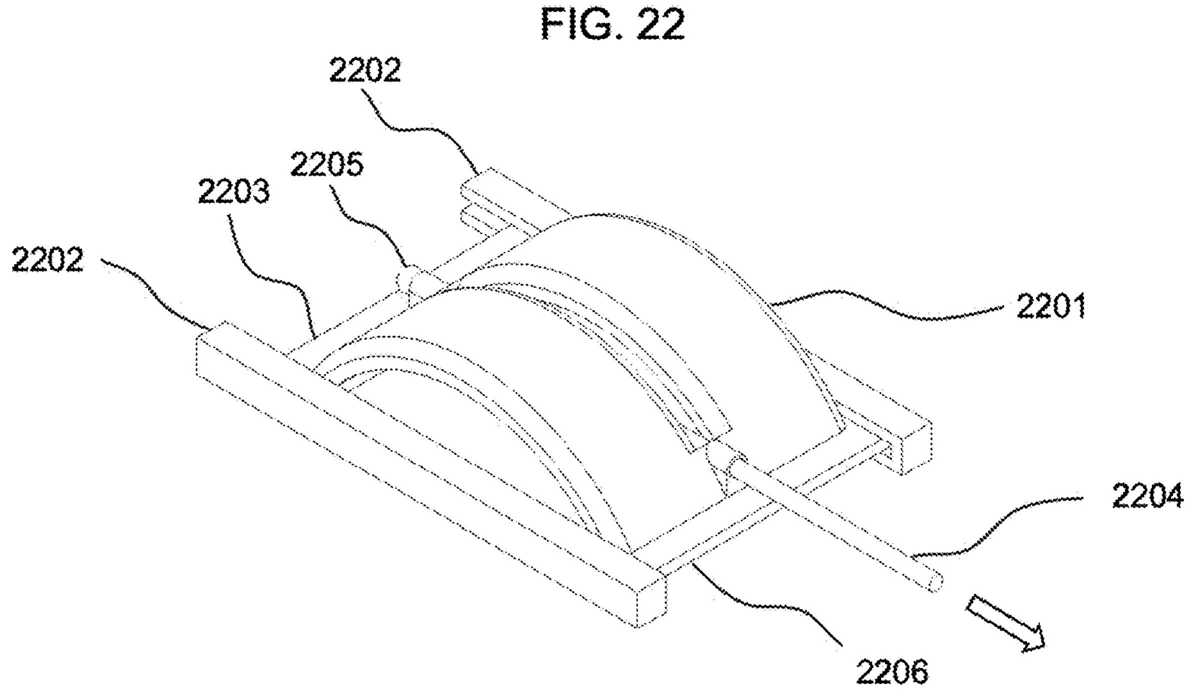
FIG. 22 illustrates an orthogonal view of a compliant version of the present invention.

FIG. 22 shows another aspect of the invention that uses a compliant material to lift one surface away from the other. Two tracks (2202) allow a guide (2203) of the compliant element (2201) to slide within the channels of the tracks. The second guide (2206) is fixed within the tracks. A tensile element (2204) is threaded through the compliant material and fixed on one end by means of a knot, crimp, ferrule, bulge, and the like (2205). When a force is applied to the tensile element in the direction of the arrow shown in FIG. 22, the upper surface of the compliant element lifts away from the surface of the tracks. The inherent elasticity of the compliant member draws itself flatter when the force is reduced to the tensile element.

The compliant element can be made from a single material or may be a combination of dissimilar materials. Likewise features such as ribs, channels, holes, patterns, and the like may be manufactured into the compliant member to alter the shape of the compliant member when it is bent.

Figure 23:
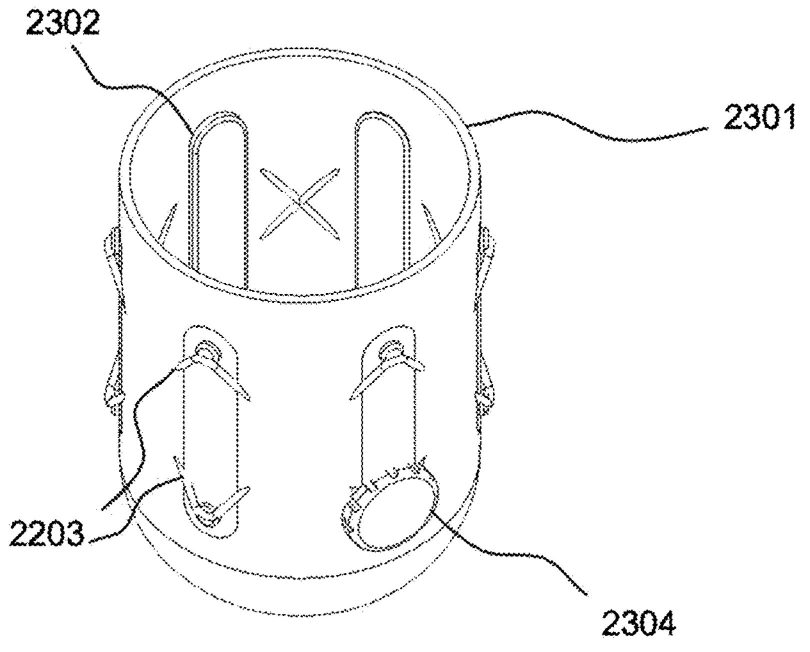
FIG. 23 is an orthogonal view of a prosthetic a composite socket comprising non-compliant and compliant elements.

FIG. 23 shows an orthogonal view of another aspect of the present invention. A prosthetic socket (2301) has a plurality of compliant sections (2302). A tensile element (2303) connects the ends of the compliant sections to one another such that when a force is applied to the tensile element by means of a tension adjustment mechanism (2304) the one end of each compliant sections moves towards the other end of each compliant section causing the middle of the compliant section to bow out towards the interior of the socket thereby reducing the volume between the worn-article (e.g., the socket) and the body part.

In aspects, the prosthetic socket (2303) could be 3D printed comprising rigid and semi rigid regions, the semi rigid regions being orthogonally compliant and capable of flexing under pressure. The complaint regions may contain spiral, or flexible membrane, collapsible ridge, or porous/mesh elements. A channel housing a tensioning element travels through a guide path within or exterior to the wall of the orthogonally complaint regions, wherein increasing tension within the tension element increases the pressure, or increases the resistance provided by the orthogonally complaint region to the limb.

In aspects, the user can adjust the volume or compression applied by the one or more compliant regions using an adjustment mechanism (e.g. a dial) to which the tensioning element is connected. In aspects, the tensioning element or compliant regions may comprise an elastomer. In aspects, the location, dimensions, resistance under load, and limit of displacement of the complaint regions may be customized to the user's limb to improve fit and distribute pressure across the limb. In aspects the compliant regions prevent localized regions of pressure and discomfort throughout the gait cycle.

In aspects, the design of the socket and position of the compliant regions and tensioning element path may be informed by pressure data collected during gait using a test socket, or input by a prosthetist, the method of which is designed to identify areas of peak pressure across the limb throughout the gait cycle.

FIG. 24 shows an orthogonal view of another aspect of the present invention. A prosthetic socket (2401) has a region (2402) where a plurality of slits have been cut and a region (2403) where the socket wall's thickness has been altered (e.g. thinned). A tensile element (2405) wraps the periphery of the socket and is attached to a tension adjustment mechanism (2404). When a force is applied to the tensile element by means of the tension adjustment mechanism, the local compliance of the slit region (2402) and the thinned region (2403) is higher than the unmodified socket and these regions flex more readily pressing inwards to reduce the volume between the worn-article and the body part.

The inventions described above may be positioned in specific areas (for example, at the condyle of the knee or at the top of a foot), may be positioned around the whole circumference of a device, or may be positioned in a spiral so that multiple laps are employed. Multiple examples may be used together within the same device for example an expandable pad at the top of the head and an expandable strap around the crown in a bicycle helmet. Various aspects of the invention could be connected in series or in parallel using several tensioning elements which converge to a single tension adjustment mechanism. Alternatively, multiple tension adjustment mechanisms may be employed to provide separate zones or areas of expansion force.

Some of the inventions depicted in the illustrations have been shown as planar assemblies for convenience, however the various elements could be curved and/or flexible to allow them to be mounted on the curved inner walls of helmets, boots, prosthetic sockets, and the like.

The inventions described above may push directly on the wearer's skin, the wearer's clothing, or on a pad, foam cutout, fabric piece, gel pad, or the like which is positioned between the lifting surfaces of the inventions and the wearer.

Other than the invention shown in FIG. 6, the inventions described above can be configured such that in the relaxed state (no applied force to the tensile element) the assembly is thin—as shown in the figures—so that applying a force expands the thickness of the assembly. In aspects, the inventions could also be configured such that in the relaxed state the assembly is expanded so that applying a force makes the assembly thinner. As a non-limited example, if the levers in FIG. 8 were standing straight (normal to the surface of the base) in their relaxed state, the tensile element could be angled such that applying a force to the tensile element would draw the tops of the levers downwards towards the base.

Alternatively, if the tensile element and spring are connected in the opposite direction (that is, the force applied by the adjustable tensioning mechanism pulls to the right with the elastic element positioned on the left of the figure) applying a force would decrease the thickness of the expandable pad or strap and relaxing the force would allow the elastic element to return the screw elements to their initial position—that being the upwards position.

In the latter configuration, the wearer would apply a force via the adjustable tensioning mechanism to collapse the pad or strap, don the device, and then reduce the force via the adjustable tensioning mechanism. The advantage of this strategy is that the strength of the elastic element would limit the compressive force generated by the expandable pad or strap and prevent 'over tightening'.

A planetary gear drive with a ratchet and pawl system could, in aspects, be used to prevent unwanted unwinding such as that disclosed in U.S. Pat. No. 11,806,264 assigned to Icarus Medical, LLC. There are times, however, when user may wish to loosen the fit of the article they are wearing without undoing the compression completely.

Figure 12:
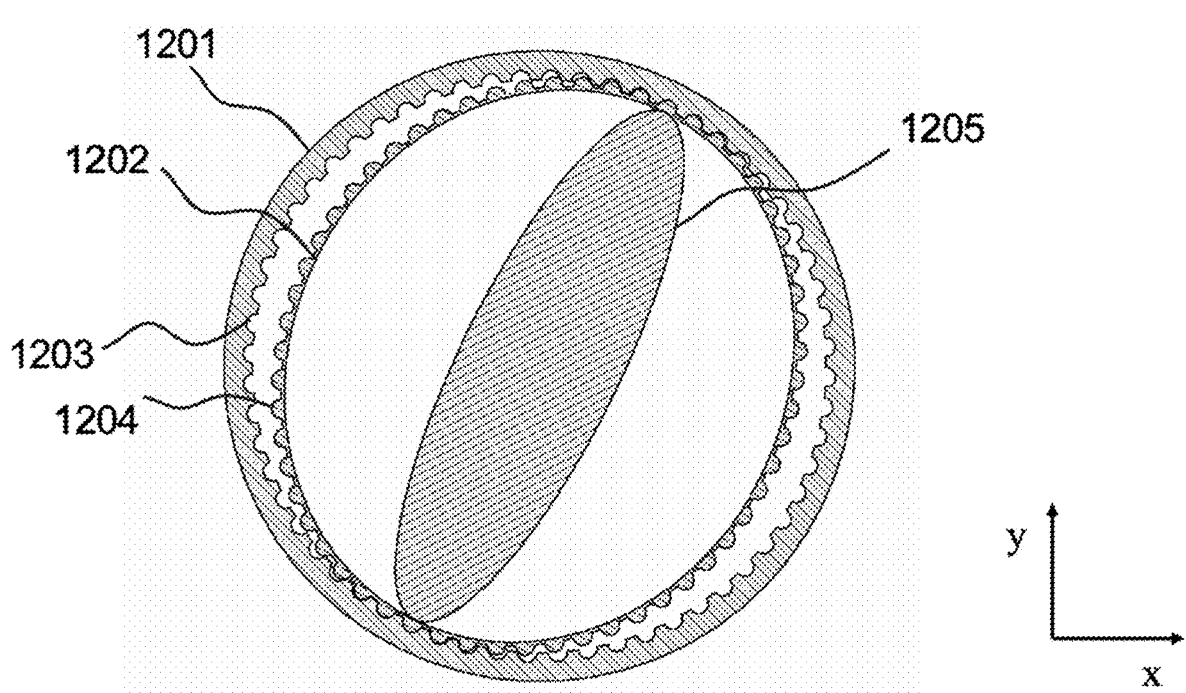
FIG. 12 is a top view of a traditional harmonic drive.

A harmonic drive is a mechanism comprising three elements: a circular spline, a flex spline, and a wave generator. FIG. 12 shows a top view of a harmonic drive. The circular spline (1201) is rigid and has teeth (1203) arrayed along the inner surface. The flex spline (1202) is flexible in the x-y plane but inflexible along the z-axis. The flex spline has teeth (1204) arrayed along the outer surface. The circumference of the flex spline is two times the width of the teeth less than the circumference of the circular spline; that is, if NFS is the number of teeth on the flex spline, NFS+2 is the number of teeth on the circular spline.

The wave generator (1205) stretches the flex spline such that the flex spline touches the circular spline along the long axis of the wave generator. The wave generator is connected to the input shaft (not shown). As the input shaft is driven clockwise, the orientation of the long axis of the wave generator also rotates clockwise which pushes the teeth of the flex spline into the levers of the circular spline. There is a slight misalignment between the crowns of the flex spline teeth and the valleys of the circular spline teeth which forces the flex spline to rotate slightly counterclockwise. The misalignment is essentially due to the difference in circumference (the width of two teeth) between the flex spline and the circular spline. After one complete revolution of the wave generator, the flex spline will rotate counterclockwise by the arc length of the width of two teeth. That is, it takes NFS turns of the wave generator to complete one full turn of the flex spline.

The wave generator shown in FIG. 12 is elliptical in shape. It has two lobes which press the flex spline into the circular spline. Increasing the number of lobes will improve the traction between the flex spline and the circular spline and will reduce the load on each flex spline tooth in contact from ½L to ⅓L. On the other hand, the height of the teeth need to be short enough that tops of the teeth do not touch at the short axes of the wave generator. With three lobed wave generators, it can become increasingly difficult to increase the number of contact points on the wave generator. For similar reasons, harmonic drives with mechanical advantage ratios less than about 30:1 are not practical. (Typically, harmonic drives are designed for 100:1 ratios or more.)

Harmonic drives have no back lash because the levers of the flex spline are in full contact with the levers of the circular spline, but harmonic drives can be back driven. With enough torque applied to the output shaft, the input shaft will rotate.

Flex splines can be made from metal in the form of a cup with very thin walls. This allows the lip of the cup to flex in the x-y plane while transmitting large values of torque around the z-axis. The cup height and wall thickness are selected such that the wave generator never plastically deforms the flex spline which would lead to failure due to strain hardening. Flex splines are still subject to fatigue, however.

Figure 13A:
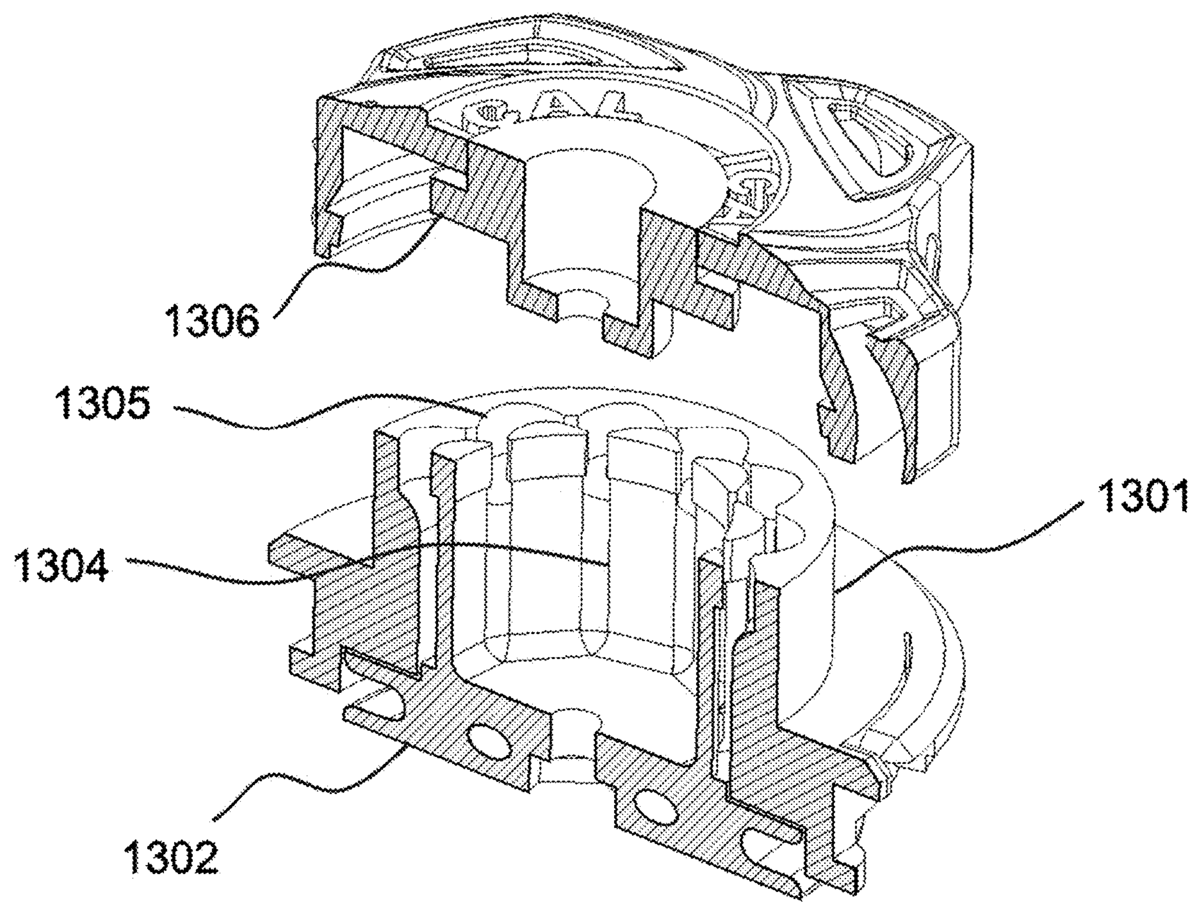
FIGS. 13*a* and 13*b* illustrate a flexible lever variant of a PhIL harmonic drive.

FIG. 13*a* shows a partially exploded orthogonal sectional view of one aspect of the harmonic drive variant of the present invention. An anchor ring (1301) which serves as the circular spline has a number, N, of notches (1305) distributed around the inner circumference. A spool (1302) which serves as the flex spline has a number of levers (1304), M, whose teeth at their tips fit into the notches. A dial rotates around the anchor ring and has a wave generator (1306) in its interior that flexes the levers of the spool and forces them to engage in the notches.

Figure 13B:
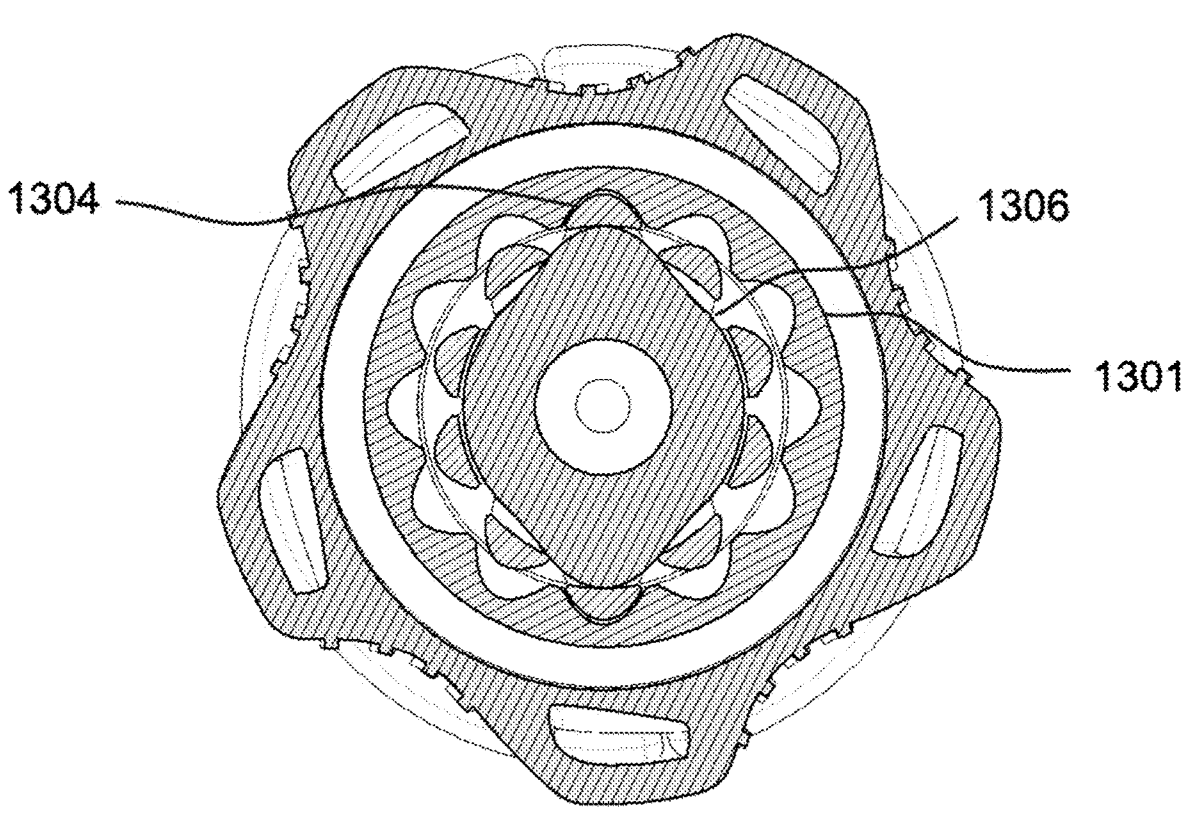

FIG. 13*b* is a top sectional view of the mechanism of FIG. 13*a* with the dial in its proper position. The wave generator portion of the dial has two lobes. These lobes push two of the levers (topmost and bottommost as viewed in FIG. 13*b*) into the two corresponding notches. The levers adjacent to these topmost and bottom most levers are partially flexed out of their equilibrium position.

The mechanical advantage of the mechanism is NLCF:1 where NLCF is N divided by the largest common factor of N and M. As shown in FIG. 13, there are 10 levers and 12 notches. The largest common factor of 10 and 12 is 2. Thus NLCF=12/2=6 and the mechanical advantage is 6:1. That is, turning the dial 6 times turns the spool 1 time.

The wave generator element of the dial pushes the toothed end of a lever of the spool into a notch in the anchor ring. Rotating the dial in the clockwise direction pushes successive levers into the corresponding notches in the anchor ring. Because there are fewer levers than notches, the circumferential distance from lever to lever is less than the circumferential distance from notch to notch. When the levers seat into the notch the spool must rotate slightly counterclockwise. Like a traditional harmonic drive, the difference in effective circumference between the flex spline and the circular spline create the mechanical advantage. Unlike a traditional harmonic drive, the levers of the present invention move independently from each other which allows a greater degree of flex in the x-y plane than a traditional harmonic drive.

Each lever element of the present invention moves in a coordinated manner as determined by the geometry of the wave generator element. The levers move in phase to contact the notches in the in the spool sequentially. This phased, sequential movement of the levers in the radial direction creates incremental rotation of the spool as the levers are pushed into notches which are slightly offset from the radial axis of each lever. This Phased, Incremental, Leverage is the basis of the harmonic drive variants described herein known collectively as PhIL harmonic drives.

The geometry of the levers shown in FIGS. 13*a* and 13*b* are generally rectangular in cross section and is similar to a beam. This allows the levers to flex readily in the radial direction but provides stiffness circumferentially. By optimizing the geometry of the levers, it is possible to make them shorter than the cup height of a traditional flex spline. Fabricating the levers from materials with good elastic properties (such as polymers) also allows the height of the levers to be significantly shorter than a traditional harmonic drive.

Figure 14:
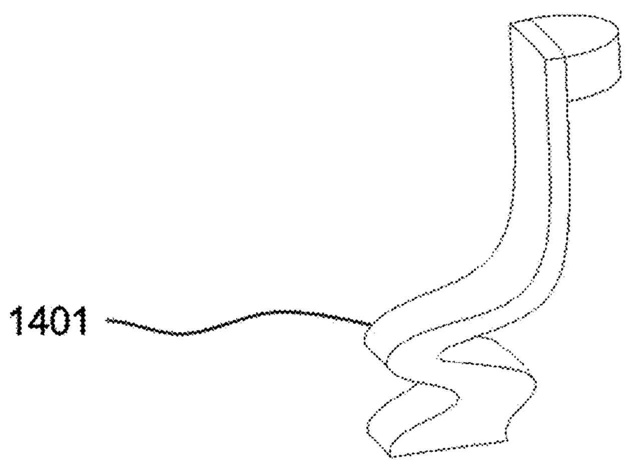
FIG. 14 shows a variant of a flexible lever suitable for a PhIL harmonic drive.

FIG. 14 shows a variation of a lever geometry suitable for a PhIL harmonic drive. The 'S' curve (1401) increases the effective length of the lever without increasing its height appreciably. In this manner, the flexibility in the radial direction is increased further allowing the height of the lever (and therefore the entire spool assembly) to be minimized.

Figure 15:
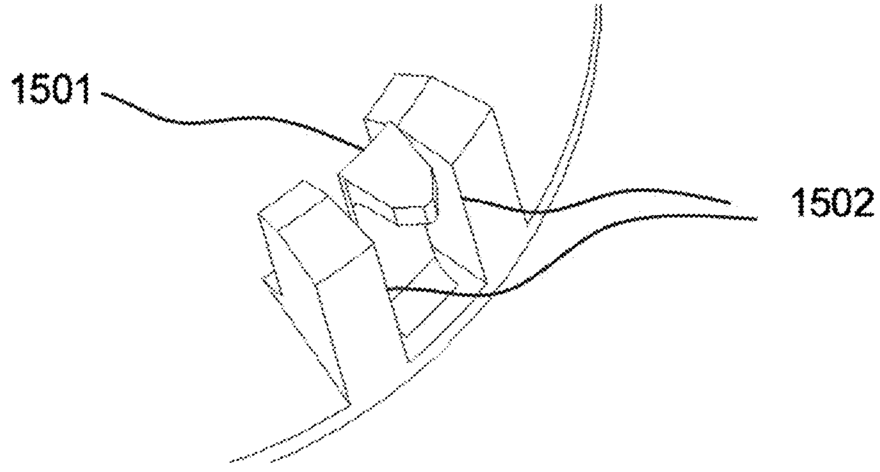
FIG. 15 shows a variant of a flexible lever with side walls suitable for a PhIL harmonic drive.

FIG. 15 shows another variation of the lever geometry of a PhIL harmonic drive. In this variation, the cross section of the lever (1501) is very thin in the radial direction to maximize flexibility. Sturdy side walls (1502) are positioned between the levers to prevent the levers from buckling under circumferential load.

The excellent flexibility of the levers in the radial direction of a PHIL harmonic drive enables the wave generator to have more lobes than a traditional harmonic drive. This is because the levers can flex in the radial direction a distance that is greater than the length of the tooth at the end of the lever (that is, the depth of the notch in the anchor ring).

FIG. 16*a* is a partially exploded orthogonal sectional view of a 3-lobe variant of an 18 lever PhIL harmonic drive. There are 18 levers (1601) attached to the spool. In the unflexed position, none of the teeth (1604) extending from the tips of the levers contact the anchor ring (1602). A trilobe wave generator (1605) is built into a dial that rotates around the anchor ring. FIG. 16*b* is a sectional top view of the PhIL harmonic drive shown in FIG. 16*a*. FIG. 16*b* clearly shows the trilobe wave generator flexing three levers into corresponding notches in the anchor ring. As the trilobe wave generator rotates in a clockwise direction, the levers (and spool) rotate in a counterclockwise direction.

The mechanical advantage of the PhIL harmonic drive shown in FIG. 16 is 7:1 which is much lower than the mechanical advantage that traditional harmonic drives can produce. Three levers are in contact with the notches and thus the torque load on any one lever is ⅓ the total torque. This is an advantage over the traditional bilobed wave generator harmonic drives where the two teeth in contact must each support ½ the total torque load. Multilobed wave generators (four, five, six, etc.) are easily accommodated by the independent flexible levers of a PHIL harmonic drive.

Like traditional harmonic drives, the wave generator can be driven either clockwise or counterclockwise which, in turn, drives the spool counterclockwise or clockwise, respectively. In practice this means that if a tensile element is affixed to the spool, the tension applied to the tensile element can be increased or decreased by turning the dial in the appropriate direction.

In theory a PhIL harmonic drive should be back-drivable just as a harmonic drive can be back driven. In practice, when the back drive torque on the spool is resolved into circumferential forces between the levers and the notches and between the back of the levers and the wave generator, those translational forces are not sufficient to overcome the friction of those components. This means that a PhIL harmonic drive, in embodiments, does not need an anti-unspooling element (such as ratchets and pawls) when it is used as the gear drive for a dial to apply tension to a flexible tensile element.

A PhIL harmonic drive is particularly well suited as the gear drive for tension adjustment mechanisms used to adjust the fit of worn articles. Turning the dial in one direction tight will apply tension tightening the fit; turning the dial in the other direction will reduce the tension loosening the fit. A clutch release mechanism or the like to fully release the tension applied to the tensile element is not required (although it could be adopted if full release of tension was desired in addition to the partial release of tension inherent in a PhIL harmonic drive). As an added benefit, because a PhIL harmonic drive does not require a ratchet and pawl system, it is silent in operation.

A PhIL harmonic drive tension adjustment mechanism would be useful for applications other than expansion mechanisms used to adjust fit as described above. A PhIL harmonic drive could be used to tightening/loosen traditional straps (such as those used to secure orthotics to the wearer's body), backpacks straps, watch straps, belts, shoes, hats, gloves, helmets and the like. While these examples have been for worn articles, a PhIL harmonic drive could be used to tighten/loosen tie down straps used to secure loads, drawn objects together (like a come-along), lift objects (like a block and tackle), etc.

A PHIL harmonic drive is useful for applications which require moderate mechanical advantage, a small footprint, silent operation, and non-back drivability. A PhIL harmonic drive does not require metal components and so would be useful in corrosive environments or for applications where metal is problematic (e.g., for applications near or inside MRI machines, metal detectors, etc.)

If the teeth at the end of the levers and the notches in the anchor ring are symmetric with respect to a plane in which the axis of rotation lies, then the PHIL harmonic drive will turn readily in either the clockwise or counterclockwise direction of the wave generator incorporated in the dial. (The spool with turn in the opposite direction of the wave generator in either case.) This could cause confusion for a user because when no tensile element is wound around the spool turning the dial in either direction will tighten the tensile element whereas the ergonomics of most mechanical devices are set up such that clockwise tightens, counterclockwise loosens. If the user of a symmetrical PHIL harmonic drive loosened the tensioning element so much that it went slack, continuing to turn the dial in the (formerly) loosening direction will actually start tightening the tensioning element.

By selecting a non-symmetric tooth/notch geometry it is possible to make a PhIL harmonic drive biased to tighten in one direction only (and correspondingly loosen in the opposite direction only). FIG. 17*a* shows a partially exploded orthogonal view non-symmetrical tooth/notch variant of a PhIL harmonic drive. This variant also shows another benefit of a PhIL harmonic drive: the flexible levers (1702) are attached to the anchor ring (1701) which is fixed. The spool (1704) rotates when the teeth (1703) at the ends of the levers, engage the notches (1705) on outer circumference of the spool. The wave generator (1707) on the interior of the dial (1706) pushes the levers radially inward instead of the traditional outwards. A PHIL harmonic drive can be configured so that the wave generator pushes the levers pushing inwards or outwards.

The teeth (1703) as shown in FIG. 17*a* are not symmetrical. A gentle arc on counterclockwise side of the tooth engages with a similar arc in the notch. On the clockwise side of the tooth, the wall is straight as is the corresponding side of the notch. FIG. 17*b* is a sectional top view of the PhIL harmonic drive shown in FIG. 17*a*. When a lever is flexed and the tooth is forced into the notch, the asymmetry biases the rotation of the spool in a counterclockwise direction. That is, turning the dial (wave generator) clockwise readily turns the spool counterclockwise. If the dial is turned counterclockwise, the straight edges on the teeth and notches do not generate any rotational offset and eventually the wave generator will rotate to a lever where the tooth is not positioned over a notch causing the dial to catch.

If the tensile element is applying some back torque to the spool, the spool will rotate backwards (in this case, clockwise) until it comes in contact with a tooth pressed inwards by the wave generator. Turning the dial counterclockwise allows the spool to rotate incrementally clockwise reducing the tension on the tensile element.

The result is that with an asymmetric tooth/notch such as the geometry shown in FIGS. 17*a* and 17*b*, when there is no tension on the tensile element the dial will turn smoothly in the clockwise direction but will catch in the counterclockwise direction. The user will naturally turn the dial clockwise to apply tension to the tensile element. Once there is tension on the tensile element, the curved arc of the spool notch will be touching the curved face of tooth of the lever that is forced inwards by the wave generator. The dial can be turned clockwise to increase the tension or counterclockwise to decrease the tension.

The notches in a PhIL harmonic drive can be wider than the width of the teeth of the levers. In some aspects, this would be a desirable feature that would allow the wave generator to gradually allow the lever to move out of the notch after it is done pushing driving the spool incrementally. Unlike a traditional harmonic drive, this geometry would allow a PhIL harmonic drive to exhibit some backlash. Backlash is not an issue for many adjustable tensioning mechanisms so this would not be a detriment.

Another variant of a PhIL harmonic drive is shown as a partially exploded orthogonal sectional view in FIG. 18*a*. A base (1801) has a plurality of channels (1802) in which levers (1803) can slide. A receiver (1804) has a plurality of notches (1805) shaped to receive the levers. There are 16 levers and 14 notches which results in an 8:1 mechanical advantage. A boss (1806) protrudes from the top surface of each lever. The wave generator is a channel (1807) which is built into a dial that rotates around the anchor ring. The bosses ride inside the channel. Rotating the dial causes the levers to slide in and out radially to sequentially engage the notches in the spool.

Unlike the previous versions of the PhIL harmonic drives shown in FIGS. 13, 16 and 17, there is no flex spline, per se. No element needs to flex; the levers engage the notches by a pure sliding action and are pushed or pulled into position by the walls of the channel. In aspects, the levers could be connected to the anchor ring by a dovetail, T-slot, or the like, which eliminates the need for channel walls and would allow the levers to be wider and spaced closer together.

FIG. 18*b* is a sectional view of the interaction between the wave generator channel and the bosses. The walls of the channel both pushes the levers into the spool and pulls them away. The force to push the levers into the spool (which causes the spool to rotate) is greater than the force needed to pull the levers away from the spool. The shape of the outer channel wall can be replicated along the inside of the dial such that the dial pushes the back of the levers directly in addition to or instead of pushing on the boss. FIG. 18*c* is a sectional view showing the corresponding positions of the lever tips interacting with the notches in the spool.

Figure 19:
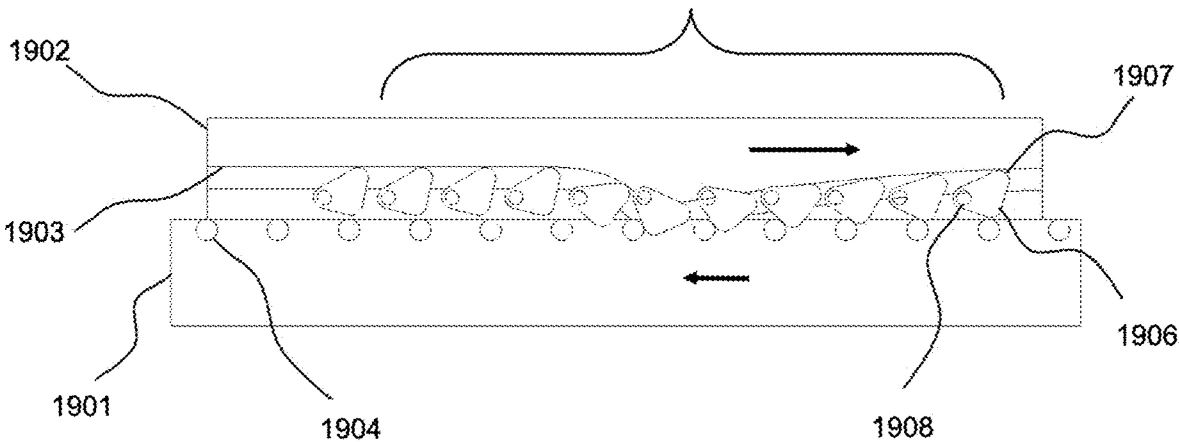
FIG. 19 shows a rotating lever variant of a PhIL harmonic drive in a linear format.

FIG. 19 is another variation of a PhIL harmonic drive. The mechanism is shown in linear format for clarity. A plurality, N, of features (1904) are connected to a base (1901). A channel (1903) is cut into a slide (1902). The track and the base are slidably attached. A plurality, M, of levers (1906) are attached to an anchor bar (not shown) by a pivot point (1908). The anchor bar does not move. Each lever has a boss (1907) that rides within the channel. A complete set of levers and features is shown by the brace at the top of the figure; there is one more lever than feature in the set. That is, $$M = N + 1$$

In FIG. 19 there are 10 levers and 9 features which will generate an 10:1 mechanical advantage.

As the slide is pushed to the right the channel causes the levers to rotate clockwise and counterclockwise in a synchronized movement. When a lever rotates clockwise it comes in contact with one of the features and pushes the feature (and the base) to the left. As the slide continues to move to the right, that lever will rotate counterclockwise and be pulled out of the way of the feature immediately to the left.

Pushing the slide to the right a distance equivalent of the width of a set causes the base to move to the left the distance between two features.

Figure 20A:
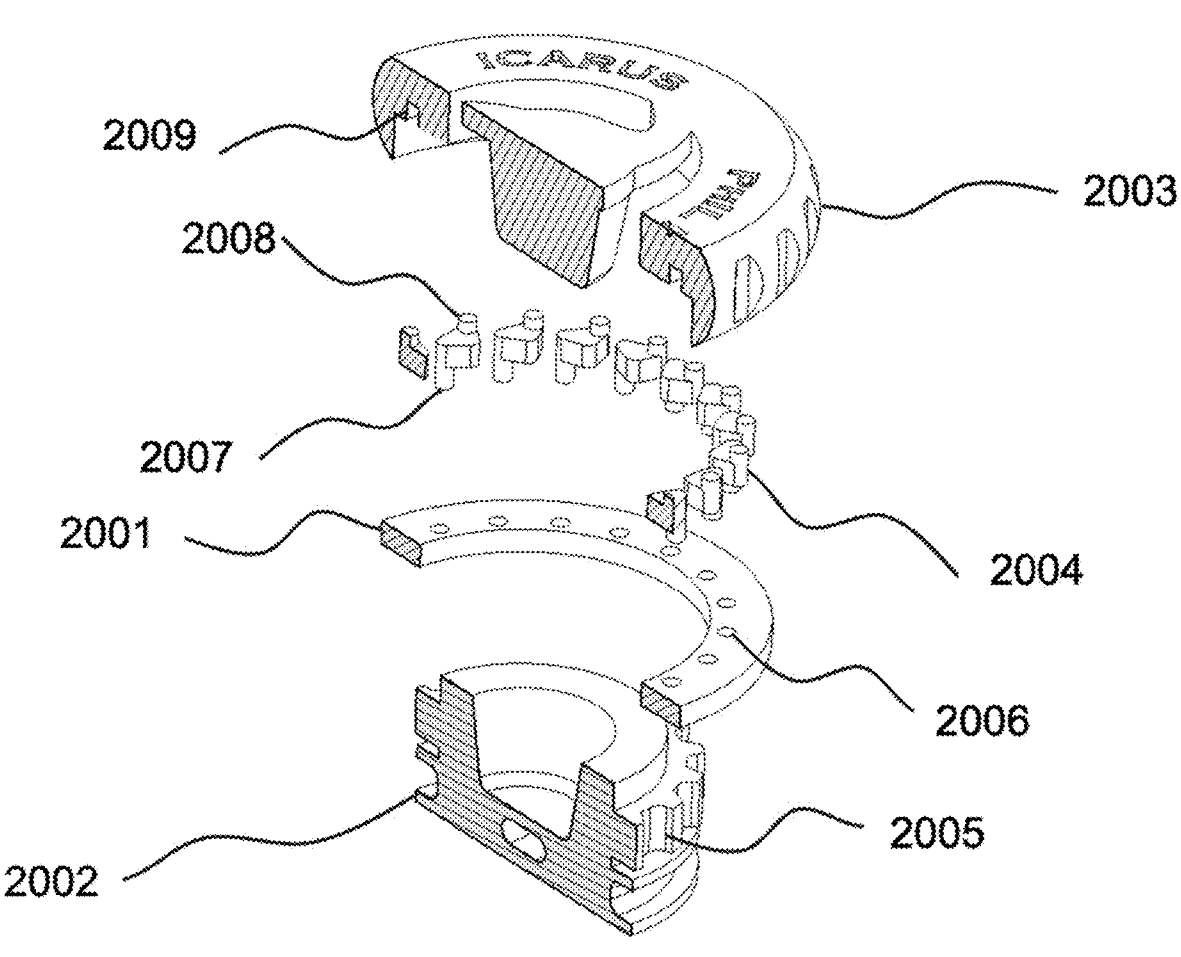

FIG. 20*a* is an exploded sectional view of a rotating lever PHIL harmonic drive. The anchor ring (2001) has pivot points (2006) distributed around its circumference. A spool (2002) rotates within the anchor ring with a plurality of features (e.g., notches) (2005) on its outer circumference. A dial (2003) rotates around the anchor ring. A plurality of levers (2004) are mounted in the anchor ring. The levers can rotate about pin (2007) inside the pivot points (2006). Each lever also has a boss (2008) which rides within a channel (2009) inside the dial.

FIGS. 20*b* and 20*c* are top sectional views of the PhIL harmonic drive shown in FIG. 20*a*. FIG. 20*b* shows a plane where the boss of the levers are riding in the dial channel. FIG. 20*c* shows a plane where the lever bodies are interacting with the features on the spool. There are 20 levers and 18 features in the device shown in FIGS. 20*a*-20*c* which results in a mechanical advantage of 10:1. The channel in the dial is a two lobed wave generator.

In the PhIL harmonic drive variants shown in FIGS. 18-20 the levers are separate pieces and not attached to anchor ring or the spool as the finger shaped levers shown in FIGS. 13-17. The large number of pieces make assembling these variants of the PHIL harmonic drive more difficult than a traditional harmonic drive which essentially has 3 main pieces: the circular spline, the flex spline, and the wave generator. FIG. 21 is a sectional view of an exploded PhIL harmonic drive that utilizes slidable levers such as shown in FIG. 18. There is a base (2101), a spool (2102), a dial (2104), and a plurality of slidable levers (2103). In this variant a small flexible element (2106) connects adjacent levers thereby collecting all the levers into a single element. The flexible element is designed so that it doesn't interfere with the ability of adjacent levers to slide substantially independently from each other. Thus, the many individual levers of previous variants can be molded or manufactured as a single element which simplifies the assembly process of a PhIL harmonic drive.

It is understood that the teeth on the levers and the notches in the spool (or anchor ring) could be swapped. That is the teeth could be disposed around the periphery of an anchor ring and notches could be placed on the ends of the levers with equivalent results. FIG. 25*a* shows a variant of a PhIL harmonic drive with notches on the ends of the levers which are connected to a base (2501) and where the corresponding teeth are disposed around the periphery of the receiver element (2502). The wave generator (not shown) flexes the levers radially inwards which cases the receiver element to rotate with respect to the base. FIG. 25*b* shows the inverse variant where the teeth are integral with the base (2503) and the levers (which are integral with the receiver (2504)) have notches on their tips corresponding to the teeth. The wave generator (not shown) flexes the levers radially outwards which causes the receiver element to rotate with respect to the base.

As shown in FIG. 19, there were no 'notches' in the base, but instead pins were connected to the base to interact with the levers. In the most general terms, the levers have features that interact with corresponding features on the spool (or anchor ring depending on whether the PhIL harmonic drive is configured with the levers to be driven inwards or outwards).

A variation of a volume-changing device (such as a prosthetic socket) may have slits or gaps in the side wall while also having a tensioning element passing through the side wall, and the tensioning element can be connected to an adjustable dial or reel. Adjusting the dial can tighten the element and cause at least one gap in the side of the socket to compress and, therefore, change the internal volume of the socket. This can also be achieved by making portions of the socket thinner than other portions, so they are more flexible and compress more easily. Another variant may have portions with materials of lower durometer than other portions, allowing the lower durometer portions to flex inward when tightening the dial. These different portions may be separate, integrated, or gradually transition from one portion to another. The devices may be 3D printed. One version of a socket can be envisioned like a web (viewed from top) or webbing connecting prongs or posts, that can compress around a residual limb. This device, and other devices described herein, can be designed through automation, and/or done either partially or totally using artificial intelligence or generative design.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entirety and as such are intended to provide an efficient way of supplementing the enabling disclosure of this invention as well as provide background detailing the level of ordinary skill in the art.

Although various features of the invention may be described in the context of a single embodiment, the features may also be provided separately or in any suitable combination. Conversely, although the invention may be described herein in the context of separate embodiments for clarity, the invention may also be implemented in a single embodiment.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including," "comprising," "consisting" and grammatical variants thereof do not preclude the addition of one or more components, features, steps, or integers or groups thereof and that the terms are to be construed as specifying components, features, steps or integers.

The invention claimed is:

1. An apparatus configured to adjust compression of a body part within a worn article, the worn article having an inner surface disposed towards the body part that defines an interior region, the apparatus comprising:

a volume-adjustable liner comprising an outer surface at least a portion of which is connected directly or indirectly to the inner surface of the worn article, and an inner surface, all or part of said inner surface of the volume-adjustable liner configured to press directly or indirectly against the body part;

a tensioning element; and an adjustable tensioning mechanism for adjusting a tension force or forces applied to the tensioning element;

wherein the tensioning element has a first portion connected to the adjustable tensioning mechanism and a second portion directly or indirectly connected to the volume-adjustable liner;

wherein about 50% or more of the second portion of the tensioning element is contained within the interior region of the worn article;

wherein adjusting the tensioning adjustment mechanism applies the tension force or forces to the tensioning element, which changes a physical volume and/or a distance between at least a portion of the inner surface of the worn article and at least a portion of the inner surface of the volume-adjustable liner, and wherein changing the physical volume or the distance is operative to compress the volume-adjustable liner directly or indirectly against the body part, thereby altering a fit of the worn article relative to the volume-adjustable liner, the body part, or both.

2. The apparatus of claim 1, wherein the change in the physical volume and/or the distance between the at least the portion of the inner surface of the worn article and the at least the portion of the inner surface of the volume-adjustable liner is reversible by reducing the tension force or forces applied to the tensioning element.

3. The apparatus of claim 2, wherein the at least the portion of the inner surface of the worn article and the at least the portion of the inner surface of the volume-adjustable liner are connected by at least one four bar linkage, and wherein the at least one four bar linkage is capable of changing the physical volume and/or the distance between the at least the portion of the inner surface of the worn article and the at least the portion of the inner surface of the volume-adjustable liner inner.

4. The apparatus of claim 2, wherein the at least the portion of the inner surface of the worn article and the at least the portion of the inner surface of the volume-adjustable liner are connected by at least one screw, and wherein the at least one screw is capable of changing the physical volume and/or the distance between the at least the portion of the inner surface of the worn article and the at least the portion of the inner surface of the volume-adjustable liner.

5. The apparatus of claim 2, wherein the at least the portion of the inner surface of the worn article and the at least the portion of the inner surface of the volume-adjustable liner are connected by at least one wedge, and wherein the at least one wedge is capable of changing the physical volume and/or the distance between the at least the portion of the inner surface of the worn article and the at least the portion of the inner surface of the volume-adjustable liner.

6. The apparatus of claim 2, wherein the at least the portion of the inner surface of the worn article and the at least the portion of the inner surface of the volume-adjustable liner are connected by at least one lever, and wherein the at least one lever is capable of changing the physical volume and/or the distance between the at least the portion of the inner surface of the worn article and the at least the portion of the inner surface of the volume-adjustable liner.

7. The apparatus of claim 2, the at least the portion of the inner surface of the worn article and the at least the portion of the inner surface of the volume-adjustable liner are connected by at least one cam, and wherein the at least one cam is capable of changing the physical volume and/or the distance between the at least the portion of the inner surface of the worn article and the at least the portion of the inner surface of the volume-adjustable liner.

8. The apparatus of claim 2, wherein the at least the portion of the inner surface of the worn article and the at least the portion of the inner surface of the volume-adjustable liner are connected by at least one set of interlaced digits, and wherein the at least one set of interlaced digits is capable of changing the physical volume and/or the distance between the at least the portion of the inner surface of the worn article and the at least the portion of the inner surface of the volume-adjustable liner.

9. The apparatus of claim 2, wherein the at least the portion of the inner surface of the worn article and the at least the portion of the inner surface of the volume-adjustable liner are connected by at least one bi-stable or multi-stable element, and wherein the at least one bi-stable or multi-stable element is capable of changing the physical volume and/or the distance between the at least the portion of the inner surface of the worn article and the at least the portion of the inner surface of the volume-adjustable liner.

10. The apparatus of claim 2, wherein the at least the portion of the inner surface of the worn article and the at least the portion of the inner surface of the volume-adjustable liner are connected by or comprise at least one compliant element, and wherein the at least one compliant element is capable of changing the physical volume and/or the distance between the at least the portion of the inner surface of the worn article and the at least the portion of the inner surface of the volume-adjustable liner.

11. The apparatus of claim 2, further comprising at least one elastic element, wherein the at least one elastic element applies a counterforce to the tensioning element, and wherein the at least one elastic element reverses the change in the physical volume and/or the distance between the at least the portion of the inner surface of the worn article and the at least the portion of the inner surface of the volume-adjustable liner.

12. The apparatus of claim 11, wherein a first end of the at least one elastic element is connected directly or indirectly to the inner surface of the volume-adjustable liner and wherein a second end of the at least one elastic element is connected to the outer surface of the volume-adjustable liner, and wherein the at least one elastic element pulls the inner surface of the volume-adjustable liner and the outer surface of the volume-adjustable liner together or pushes the inner surface of the worn article and the inner or outer surface of the volume-adjustable liner.

13. The apparatus of claim 11, wherein the at least one elastic element is in-line with the tensioning element.

14. The apparatus of claim 2, wherein the at least the portion of the inner surface of the worn article and the at least the portion of the inner surface of the volume-adjustable liner, the adjustable tensioning mechanism, the tensioning element, or combinations thereof, are manufactured together as a single article.

15. The apparatus of claim 1, wherein the worn article is a prosthetic socket.

16. The apparatus of claim 1, wherein the adjustable tensioning mechanism, the tensioning element, or combinations thereof, provide both a separating force to increase the distance between the at least a portion of the inner surface of the worn article and the at least the portion of the inner surface of the volume-adjustable liner and a translational force substantially parallel to the at least the portion of the inner surface of the volume-adjustable liner.

17. The apparatus of claim 1, wherein applying the tension force or forces to the tensioning element increases the physical volume and/or the distance between the at least the portion of the inner surface of the worn article and the at least the portion of the inner surface of the volume-adjustable liner.

18. The apparatus of claim 1, wherein applying the tension force or forces to the tensioning element decreases the physical volume and/or the distance between the at least the portion of the inner surface of the worn article and the at least the portion of the inner surface of the volume-adjustable liner.

19. The apparatus of claim 1, further comprising one or more sensors to monitor the fit of the worn article and/or to provide sensor information to a processor, the processor operative to directly or indirectly activate a motor to automatically adjust the tension force or forces applied to the tensioning element.

20. The apparatus of claim 1, wherein the tensioning adjustment mechanism allows the wearer of the apparatus to adjust the fit of the worn article by increasing or decreasing the tension force or forces applied to the tensioning element.

21. The apparatus of claim 1, wherein the at least the portion of the inner surface of the volume-adjustable liner is semi-rigid or flexible, and wherein by increasing the tension force or forces applied to or within the tensioning element, the at least the portion of the inner surface of the volume-adjustable liner distributes a substantially uniform pressure across a region of the body part on which the apparatus is worn.

22. The apparatus of claim 1, further comprising at least one pulley system, wherein the at least one pulley system allows for the tensioning element to be redirected, or to provide a mechanical advantage, within the interior region, outside the interior region, or combinations thereof.

23. A system device for modifying an interior volume of a worn article, the worn article having an inner surface that defines an interior region: wherein modifying the interior volume adjusts a fit of the worn article to a body part, wherein the system includes at least one wall disposed within the interior region, wherein the at least one wall comprises at least one rigid section and at least one compliant section, wherein at least one tensioning element directly or indirectly connects the at least one compliant section to the at least one rigid section, such that when a force is applied to the tensioning element using a tension adjustment mechanism, the at least one compliant section is forced to bow inward, causing it to reduce a distance between the at least one wall and the body part.

24. The system device of claim 23, wherein the at least one compliant section and the at least one rigid section are continuous.

25. The system device of claim 23, wherein the compliant section comprises slots and/or spaces that allow the at least one wall to move inward towards the body part as tension is increased in the tensioning element.

* * * * *